(12) United States Patent
Schüle et al.

(10) Patent No.: US 10,500,686 B2
(45) Date of Patent: Dec. 10, 2019

(54) DENTAL MILLING MACHINE

(71) Applicant: vhf camfacture Aktiengesellschaft, Ammerbuch (DE)

(72) Inventors: Florian Schüle, Tübingen (DE); Matthias Breil, Radolfzell (DE)

(73) Assignee: vhf camfucture Aktiengesellschaft, Ammerbuch (DE)

( * ) Notice: Subject to any disclaimer, the term of this patent is extended or adjusted under 35 U.S.C. 154(b) by 0 days.

(21) Appl. No.: 15/885,842

(22) Filed: Feb. 1, 2018

(65) Prior Publication Data
US 2018/0236620 A1  Aug. 23, 2018

(30) Foreign Application Priority Data

Feb. 3, 2017  (DE) .......................... 10 2017 001 278

(51) Int. Cl.
| | |
|---|---|
| *B23Q 7/04* | (2006.01) |
| *B23Q 3/06* | (2006.01) |
| *A61C 13/00* | (2006.01) |
| *B23Q 7/10* | (2006.01) |
| *A61C 1/00* | (2006.01) |

(52) U.S. Cl.
CPC ............... *B23Q 3/062* (2013.01); *A61C 1/00* (2013.01); *A61C 13/0022* (2013.01); *B23Q 7/043* (2013.01); *B23Q 7/047* (2013.01); *B23Q 7/10* (2013.01)

(58) Field of Classification Search
CPC ...... A61C 13/0022; A61C 1/00; B23Q 3/062; B23Q 7/043; B23Q 7/047; B23Q 7/10

USPC .............. 409/134, 212, 202, 135, 136, 137; 269/60, 55, 143, 249, 71, 47, 289 R
See application file for complete search history.

(56) References Cited

U.S. PATENT DOCUMENTS

| | | | | |
|---|---|---|---|---|
| 3,825,245 A | * | 7/1974 | Osburn ................ | B23Q 7/1431 198/346.1 |
| 4,480,738 A | * | 11/1984 | Mattson ............... | B23Q 7/1431 198/346.1 |
| 4,519,733 A | * | 5/1985 | Gregg ..................... | B23F 23/04 198/346.2 |
| 4,644,635 A | * | 2/1987 | Murai ...................... | B23Q 1/54 269/71 |

(Continued)

FOREIGN PATENT DOCUMENTS

WO  WO-9208420 A1 * 5/1992 ......... A61C 13/0009

*Primary Examiner* — Nicole N Ramos
(74) *Attorney, Agent, or Firm* — Gudrun E. Huckett

(57) ABSTRACT

A dental milling machine has idle receptacles arranged in a storage chamber for storing a plurality of blanks. The blanks each are placed without frame as a frameless blank in the idle receptacles. A transfer device with a transport arm is arranged in the storage chamber. A work chamber adjoins the storage chamber. A transfer opening is arranged between work chamber and storage chamber. The transport arm grips a frameless blank stored in the storage chamber and moves it through the transfer opening into the work chamber. A workpiece holder arranged in the work chamber receives the frameless blank from the transport arm. The workpiece holder grips the frameless blank by a receiving rim of the frameless blank. The workpiece holder, for milling the frameless blank in the work chamber by a milling tool, holds by a clamping action the frameless blank at the receiving rim.

20 Claims, 17 Drawing Sheets

(56) References Cited

U.S. PATENT DOCUMENTS

| | | | | |
|---|---|---|---|---|
| 4,809,422 | A * | 3/1989 | Kitamura | B23Q 1/4857 29/33 P |
| 5,704,262 | A * | 1/1998 | Baumbusch | B23B 3/30 82/124 |
| 5,781,983 | A * | 7/1998 | Gruner | B23Q 7/047 29/33 P |
| 6,634,265 | B2 * | 10/2003 | Yasuda | B23Q 7/005 82/122 |
| 7,013,544 | B2 * | 3/2006 | Yasuda | B23Q 7/1431 29/27 C |
| 7,192,225 | B2 * | 3/2007 | Takayama | B23Q 11/0816 409/134 |
| 7,682,223 | B2 * | 3/2010 | Wirz | B23F 23/04 451/11 |
| 9,242,327 | B2 | 1/2016 | Evertz et al. | |
| 2010/0018836 | A1 * | 1/2010 | Kikkawa | B23Q 7/1431 198/339.1 |
| 2011/0280692 | A1 * | 11/2011 | Evertz | B23Q 7/047 414/222.07 |
| 2013/0216323 | A1 * | 8/2013 | Reck | B23Q 1/5437 483/56 |
| 2013/0244846 | A1 * | 9/2013 | Koch | A61C 13/0003 483/16 |
| 2015/0174716 | A1 * | 6/2015 | Suyama | B23Q 3/06 409/225 |

* cited by examiner

DENTAL MILLING MACHINE

BACKGROUND OF THE INVENTION

The invention concerns a dental milling machine comprising a workpiece holder, provided in a work chamber, for a blank that is to be machined in the work chamber by means of a milling tool. A storage chamber adjoining the work chamber is provided for a multitude of blanks to be machined wherein a transfer opening is provided between the work chamber and the storage chamber. A blank to be machined is moved from the storage chamber through the transfer opening into the work chamber.

Such a dental milling machine is disclosed in U.S. Pat. No. 9,242,327 B2. In a work chamber within the housing of the dental milling machine, a workpiece holder for a blank is provided which is to be machined in the work chamber by means of a milling tool. In a storage chamber adjoining the work chamber, a multitude of blanks to be machined are stored wherein, between the work chamber and the storage chamber, a transfer opening is provided through which a blank to be machined is moved from the storage chamber into the work chamber.

For exchanging a blank, the workpiece holder moves through the transfer opening into the storage chamber and places the blank, which is clamped in a frame, into a receiving rotor which is provided with a multitude of blanks held in frames.

Loading of the storage chamber with blanks to be machined thus requires for each blank a frame in which the blank must be clamped prior to loading into the storage chamber. This is time-consuming and labor-intensive.

The invention has the object to configure a dental milling machine with a work chamber and a storage chamber in such a way that blanks to be machined can be loaded quickly and without additional preparation work into the storage chamber.

SUMMARY OF THE INVENTION

As a solution to the object, a dental milling machine is proposed comprising a workpiece holder, provided in a work chamber, for a blank wherein the blank is to be machined by a milling tool in the work chamber. The dental milling machine comprises a storage chamber, adjoining the work chamber, for a multitude of blanks to be machined wherein, between the work chamber and the storage chamber, a transfer opening is provided and a blank to be machined is moved from the storage chamber through the transfer opening into the work chamber. A plurality of blanks to be machined are placed without frame in idle receptacles of the storage chamber. In the storage chamber, a transfer device with a transport arm is arranged wherein the transport arm grips a frameless blank to be machined in the storage chamber and moves it through the transfer opening into the work chamber. In the work chamber, the workpiece holder grips the frameless blank by a receiving rim and, for processing by milling, the frameless blank is held, clamped at its receiving rim, in the workpiece holder.

Without having to arrange frames, the blanks to be machined are thus inserted without frame into the storage chamber, for which purpose simple idle receptacles for positioning and holding the frameless blanks are provided in the storage chamber.

Advantageously, the storage chamber is provided below the work chamber so that the width of the dental milling machine can be kept minimal.

The idle receptacles for the frameless blanks are provided on a carousel plate of a receiving carousel arranged in the storage chamber, whereby the blanks provided for machining can be moved into the gripping range of the transport arm in a simple way by rotation of the carousel plate. For this purpose, it is expedient that the receiving carousel can be rotated about an axis of rotation which is embodied as a vertical axis.

An idle receptacle for a frameless blank is advantageously provided as a semi-circular receiving shell for upright reception of a frameless blank. Due to the upright reception, the blank can be gripped in a simple way by the transport arm.

The idle receptacle is advantageously formed as a U-shaped frame. At least one leg of the U-shaped frame is pivotable so that the receiving shell of the idle receptacle can be opened to the front. In this way, a simple loading of the idle receptacle is possible.

Expediently, the transport arm grips by means of holders a receiving rim of the blank, clamps securely the receiving rim between the holders, and lifts it, in particular vertically, out of the idle receptacle. Expediently, the transport arm moves vertically from above the idle receptacle toward a frameless blank that is to be gripped. The transport arm grips the blank and lifts the blank vertically out of the idle receptacle. Subsequently, the transport arm pivots together with the frameless blank into a horizontal position for transfer of the blank to the workpiece holder. Upon pivoting of the transport arm into the horizontal position, the changeover flap of the transfer opening is opened at the same time so that the connection between the receiving chamber and the storage chamber is open.

Upon transfer to the workpiece holder for machining the frameless blank, a receiving rim provided at its outer circumference is held by clamping action between clamping jaws of the workpiece holder. Advantageously, at least one clamping spring is arranged between the clamping jaws of the workpiece holder for applying a clamping force. For canceling the clamping force, the clamping force of the spring acting between the clamping jaws is equalized by a controlled counterforce wherein, in a particular way, the counterforce is a pneumatic force acting through a piston and oriented opposite to the spring force. The piston is part of a pneumatic cylinder which moves a movable clamping jaw embodied as a clamping claw relative to the stationary clamping jaw.

Advantageously, for actuation of the clamping claw, at least one actuating cylinder for the clamping claw, a guiding element for the clamping claw, and a force storage device for the clamping claw are provided in the stationary clamping jaw of the workpiece carrier. In a special embodiment of the invention, the actuating cylinder, the guiding element, and the force storage device are component groups that are functionally separate from each other. Expediently, each actuating cylinder has at least one guiding element and at least one force storage device assigned thereto in this context.

In particular, the clamping claw can be actuated, guided, and held by a plurality of actuating cylinders, a plurality of guiding elements, and a plurality of force storage devices. Canting of the clamping claw can be avoided.

In order to ensure a disturbance-free, uniform clamping action by the clamping claw, the plurality of guiding elements are positioned on a first common circular arc with a first diameter and the plurality of force storage devices on a second common circular arc with a second diameter. The first diameter is different from the second diameter so that between the circular arcs an annular section is formed. In this annular section between the circular arcs, the actuating cylinders are arranged. Advantageously, the arrangement is such that two guiding elements and two force storage devices are arranged, respectively, in the spatial area between two actuating cylinders.

BRIEF DESCRIPTION OF THE DRAWINGS

Further features of the invention result from the additional claims, the description, and the drawing in which an embodiment of the invention, described in the following in detail, is illustrated.

DESCRIPTION OF THE PREFERRED EMBODIMENTS

Figure 1:
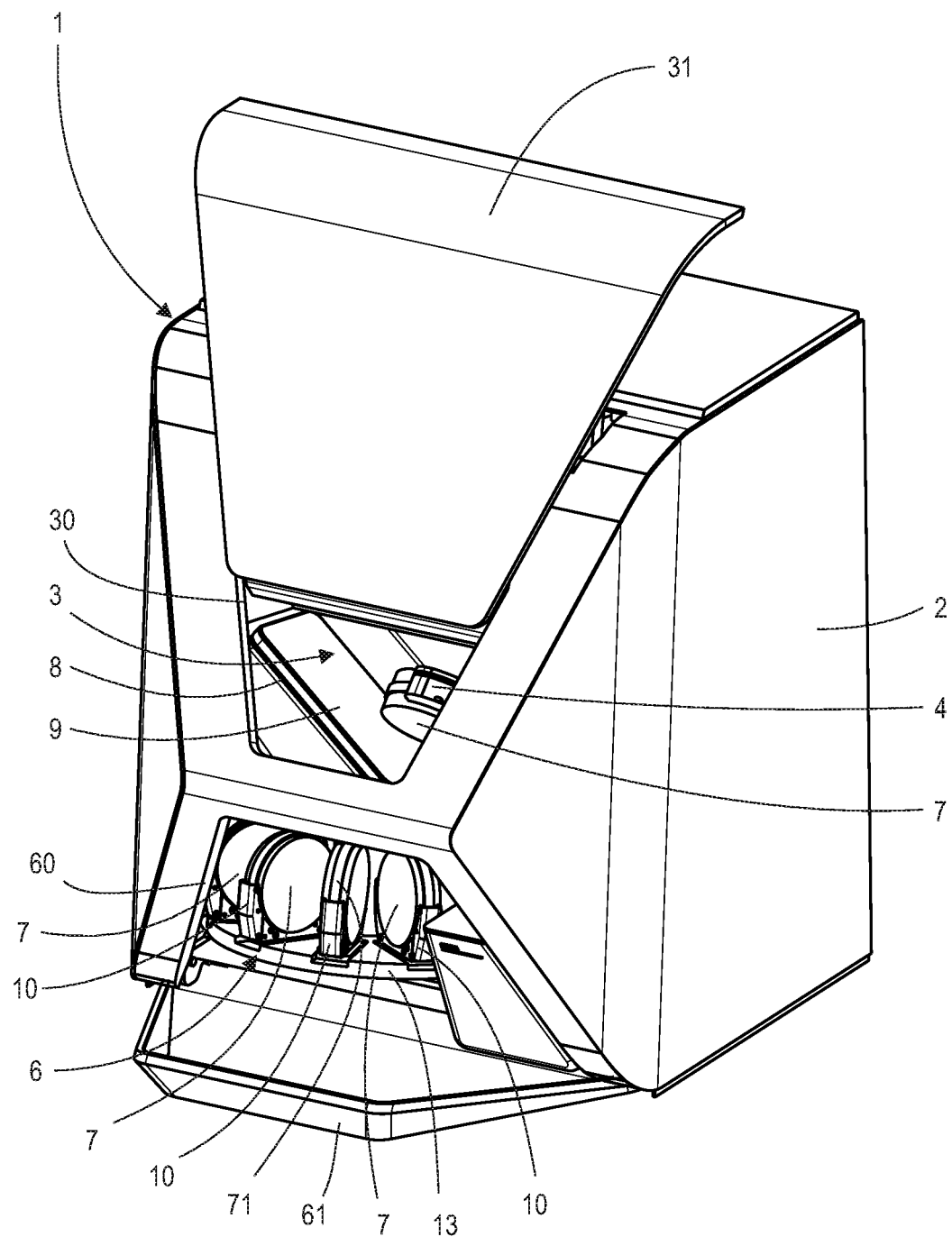
FIG. 1 shows a dental milling machine with open work chamber and open storage chamber.
Figure 2:
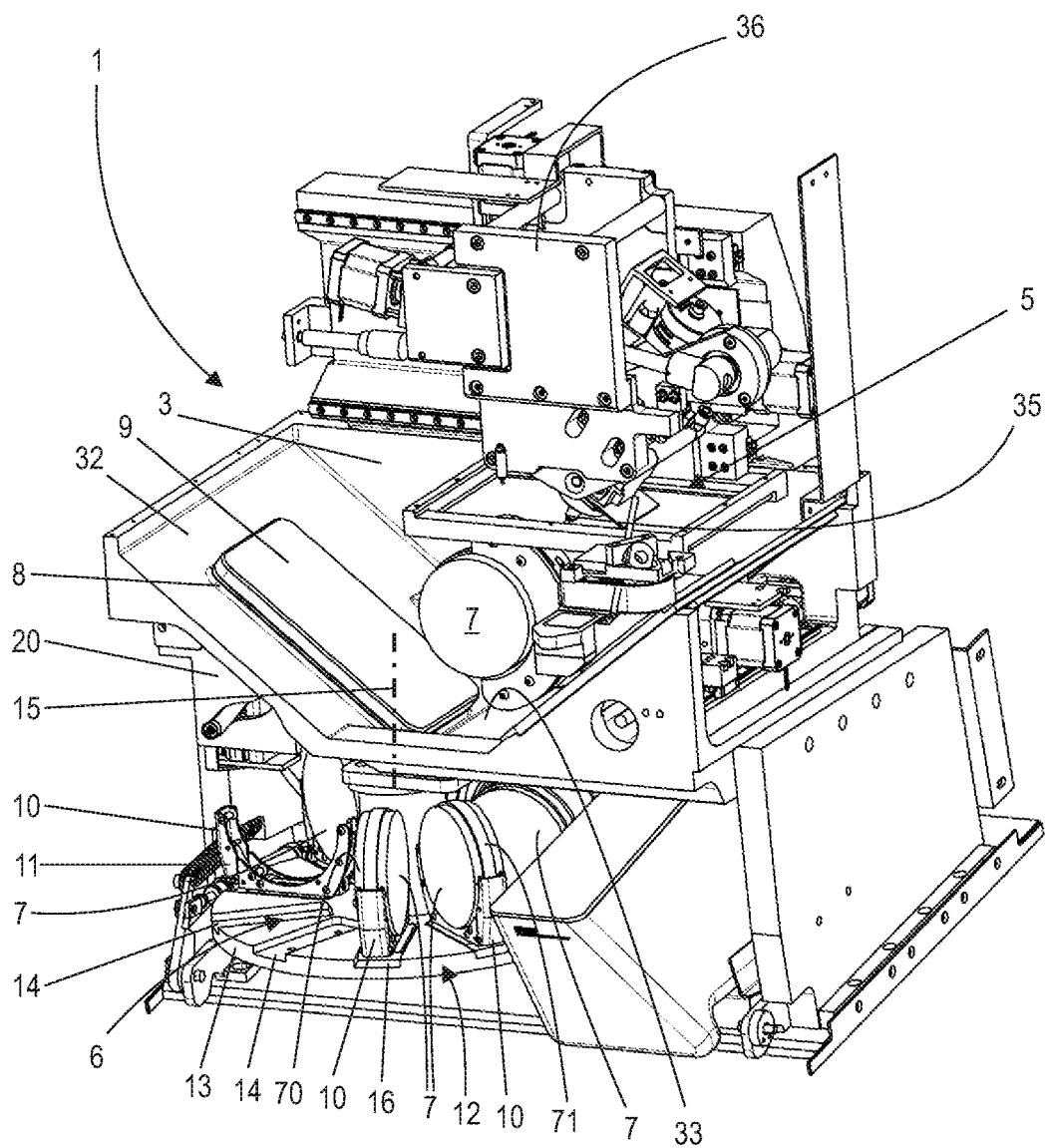
FIG. 2 shows the dental milling machine according to FIG. 1 without housing.
Figure 3:
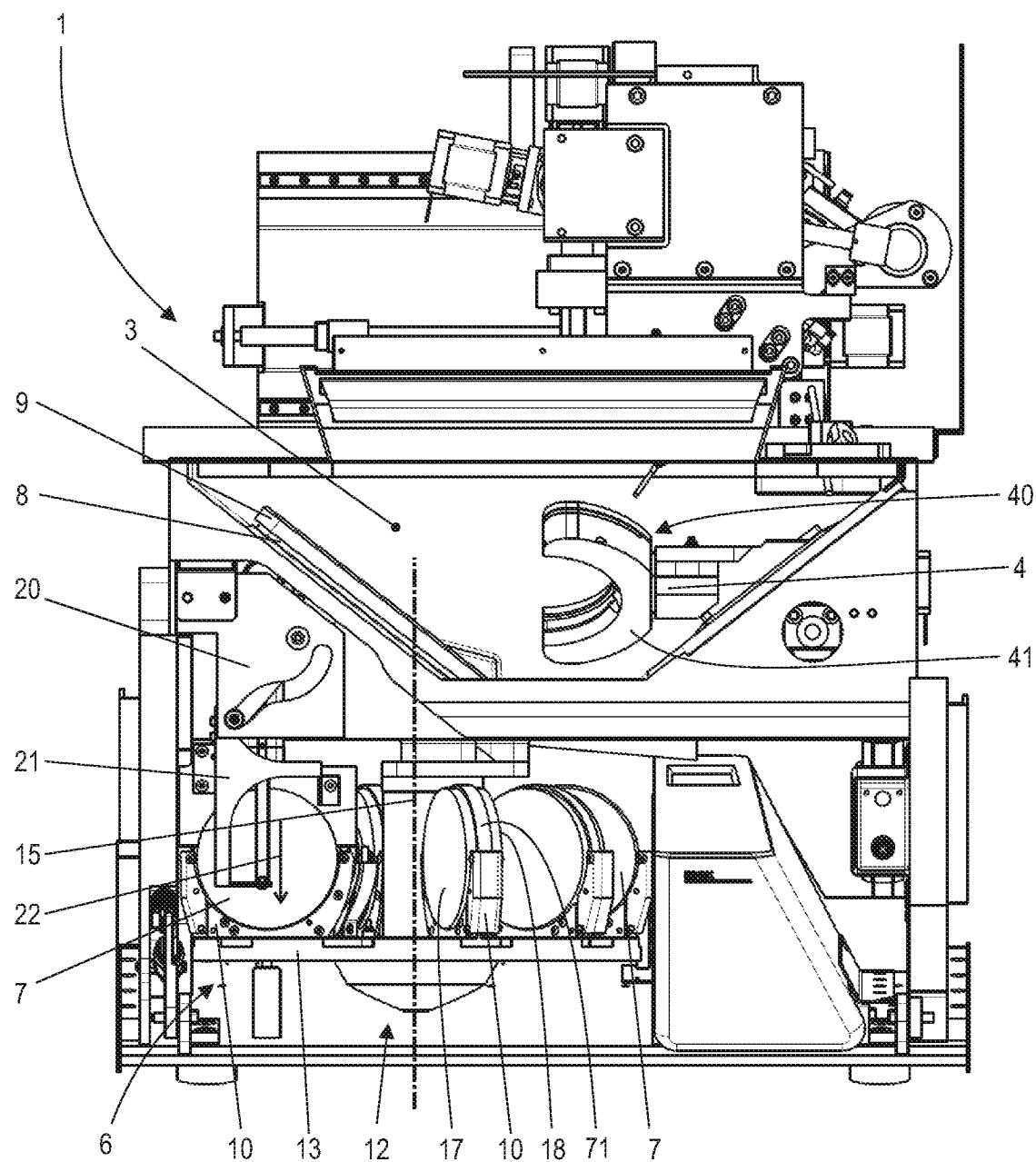
FIG. 3 shows a view of the dental milling machine according to FIG. 2 with a transport arm that has been moved toward a frameless blank.
Figure 4:
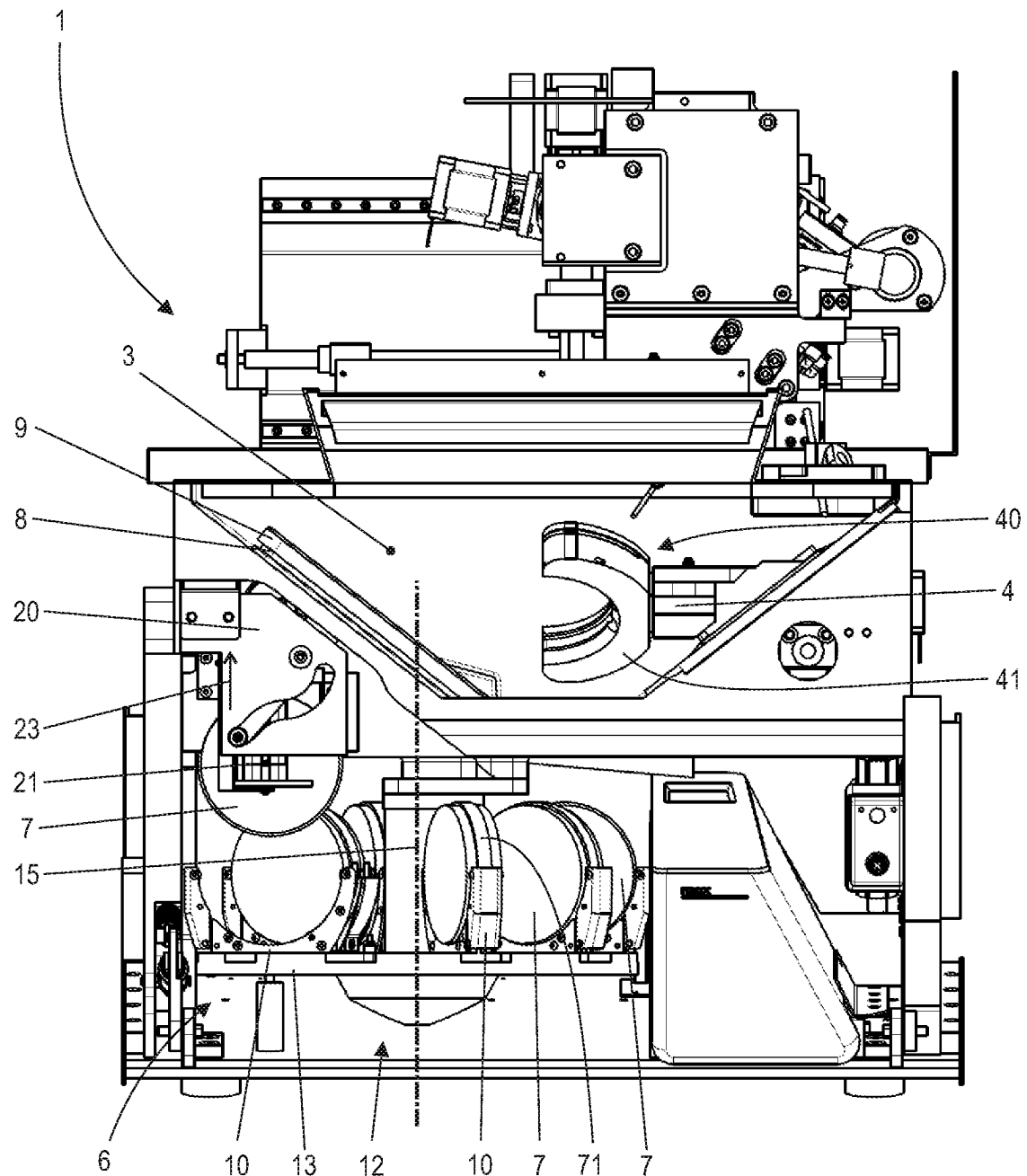
FIG. 4 shows an illustration according to FIG. 3 with the blank lifted by the transport arm out of the idle receptacle.

The dental milling machine 1 according to FIG. 1 comprises a housing 2 in which a work chamber 3 with a workpiece carrier 4 and a milling assembly 5 (FIG. 2) is arranged. The work chamber 3 is a work chamber closed on all sides so that dust, cuttings or the like cannot escape in an uncontrolled fashion to the exterior.

Below the work chamber 3, a storage chamber 6 is embodied which receives a plurality of frameless blanks 7 to be machined. Between the work chamber 3 and the storage chamber 6 a transfer opening 8 is embodied which is closed by a changeover flap 9. The changeover flap 9 is arranged such that it opens into the work chamber 3.

After opening a door 31, the work chamber 3 is accessible through an access opening 30 from the exterior of the housing 2. Correspondingly, the storage chamber 6 comprises an access opening 60 that is to be closed off by a loading flap 61. Through the access opening 60 of the storage chamber 6, frameless blanks 7 to be machined are manually inserted into the storage chamber 6, in particular by an operator.

The storage chamber 6 is embodied within the housing 2 of the dental milling machine 1 below the work chamber 3 wherein idle receptacles 10 are provided for receiving the frameless blanks 7. An idle receptacle 10 is designed as a semi-circular receiving shell 11 which surrounds a frameless blank 7 up to half of its outer circumference 70. Preferably, the semi-circular receiving shell 11 surrounds less than half of the circumference of the outer circumference 70 of a frameless blanks 7.

As shown in FIGS. 2 through 7, the idle receptacles 10, formed as receiving shells 11, for frameless blanks 7 are arranged on a receiving carousel 12. The receiving carousel 12 is comprised of a carousel plate 13 in which depressions are formed as radial base receptacles 14. Each base receptacle 14 is positioned radially relative to the axis of rotation 15 of the receiving carousel 12. The base receptacles 14 are milled as T-grooves into the carousel plate 13 and serve for receiving a support base 16 that is formed on the idle receptacle 10. The support base 16 of an idle receptacle 10 is inserted into the base receptacle 14 and locked therein, preferably by a resilient pressure member or the like. It can be provided to insert a blank 7 outside of the storage chamber 6 of the dental milling machine 1 into a idle receptacle 10 and to place the thus loaded idle receptacle 10 on the carousel plate 13.

Idle receptacles 10 for blanks 7 of different dimensions can be arranged in an easily exchangeable way on the carousel plate 13 of the receiving carousel 12.

In the storage chamber 6, a transfer device 20 with a transport arm 21 (FIG. 3) is moreover provided which, as shown in FIGS. 3 to 6, grips a frameless blank 7 in the storage chamber 6 and feeds it to the workpiece carrier 4. For this purpose, in the bottom 32 of the work chamber 3 a transfer opening 8 is embodied which can be closed by an changeover flap 9 in the work chamber. As can be seen in particular in FIGS. 2 through 4, the bottom 32 of the work chamber 3 is of a V-shaped design so that cuttings produced during machining are discharged to a cuttings discharge groove 33.

For loading the workpiece carrier 4, the transport arm 21 of the transfer device 20 moves vertically from above an idle receptacle 10 in the direction of arrow 22 toward a frameless blank 7 and grips the latter. In this context, the transport arm 21 can grip a receiving rim 71 surrounding expediently the outer circumference 70 of a blank 7 in order to lift a blank 7 out of an idle receptacle 10. It can also be advantageous when the transport arm 21 engages the end faces 17, 18 of a frameless blank 7 with holders in order to hold the blank 7 by clamping action and lift it out of the idle receptacle 10.

Figure 5:
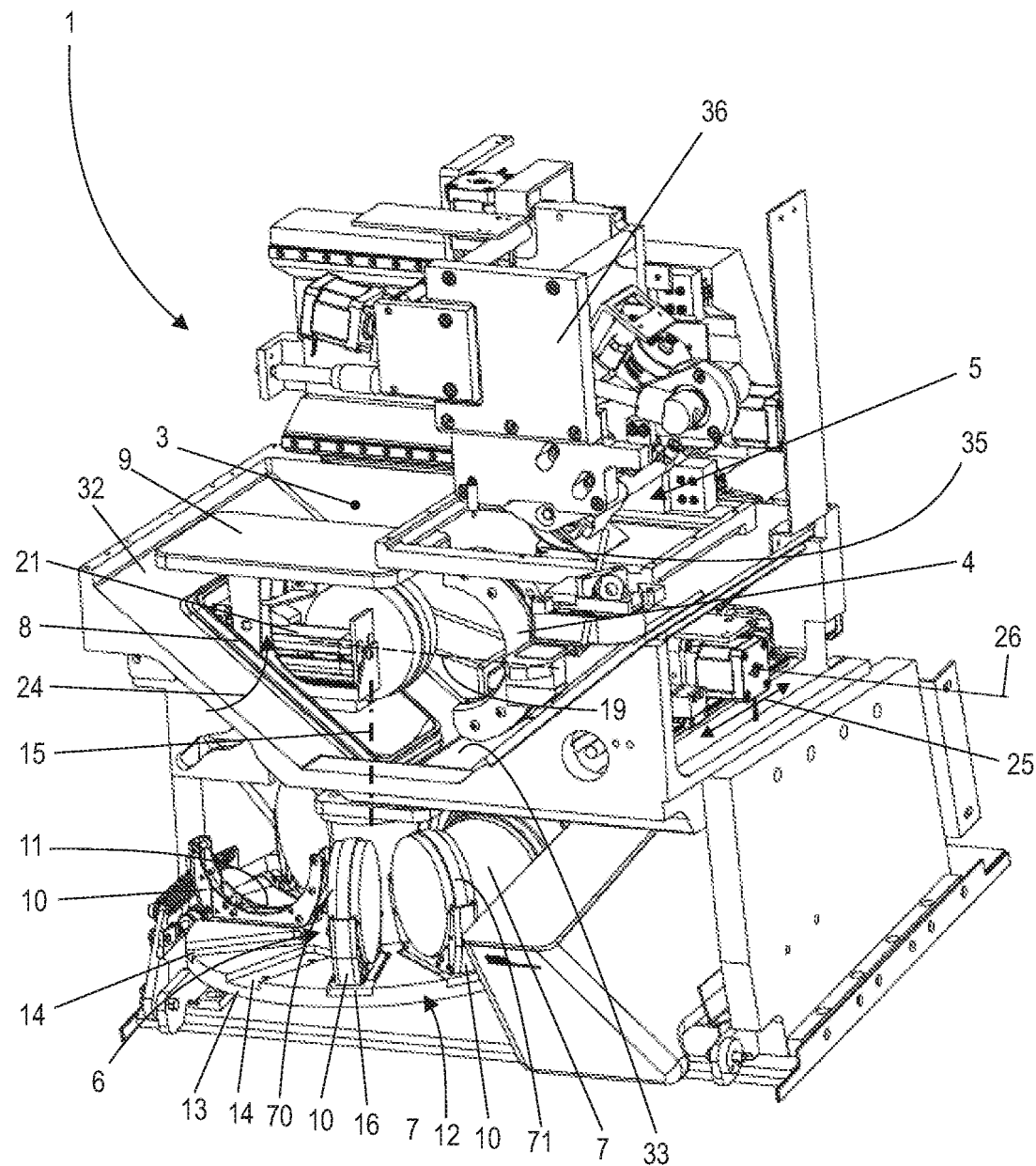
FIG. 5 shows an illustration according to FIG. 3 with a transport arm pivoted about 90° and projecting into the work chamber.

Once the blank 7 has been gripped by the transport arm 21, the blank is lifted in the direction of arrow 23 (FIG. 4) out of the idle receptacle 10 of the receiving carousel 12. Once the blank 7 has been moved away from the idle receptacle 10, the transport arm 21 pivots in the direction of arrow 24 out of the vertical into the horizontal, as indicated in FIG. 5. With the pivot movement of the transport arm 21, the changeover flap 9 of the transfer opening 8 opens; the changeover flap 9 closing off the transfer opening 8 pivots into the work chamber 3 (FIG. 5). The transfer opening 8 between the storage chamber 6 and the work chamber 3 is open.

In the horizontal position of the transport arm 21 illustrated in FIG. 5, the transport arm 21 is positioned approximately coaxial to a common longitudinal axis 19 of workpiece carrier 4 and transport arm 21. The workpiece carrier 4 can be moved in the direction of double arrow 25 transverse to the transport arm 21 and pivoted about an axis of rotation 26 until the workpiece carrier 4 is aligned in a transfer position relative to the transport arm 21 or relative to the blank 7 held by the transport arm 21.

Figure 6:
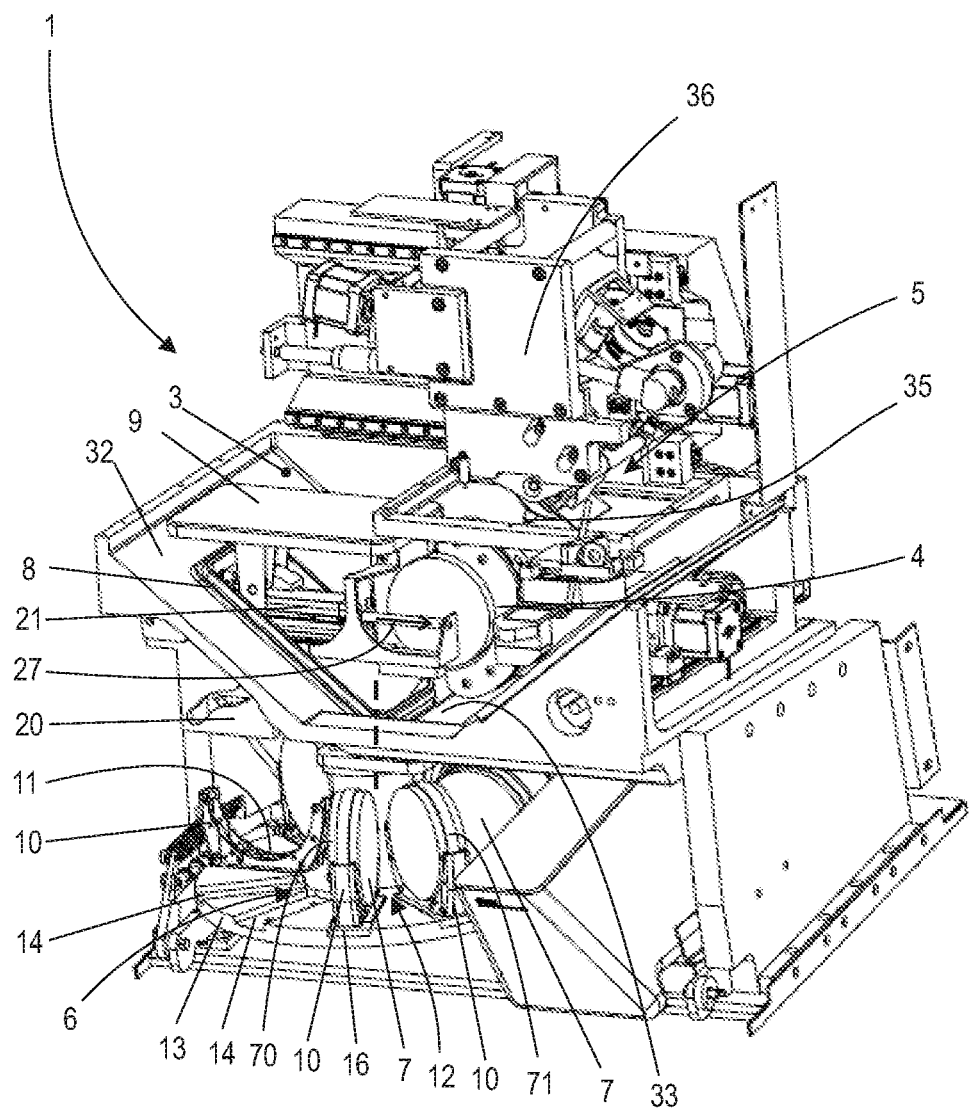
FIG. 6 shows an illustration according to FIG. 3 with the transport arm positioned in transfer position in front of the workpiece holder.
Figure 7:
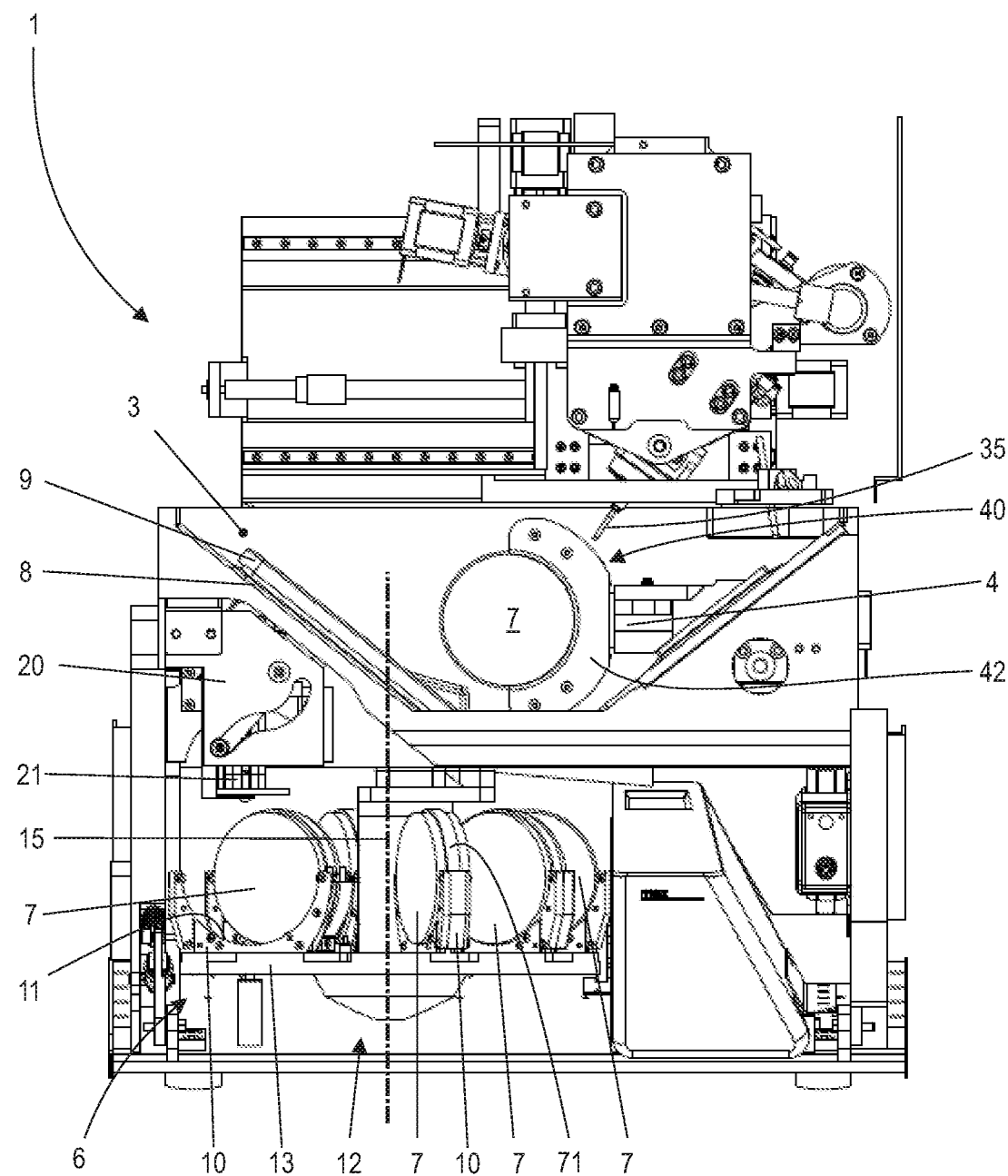
FIG. 7 shows an illustration according to FIG. 3 with the transport arm returned into the storage chamber and blank clamped in the workpiece carrier.

Once the workpiece carrier 4 is aligned relative to the position of the frameless blank 7 at the transport arm 21, the transport arm 21 moves in the direction of arrow 27 toward the workpiece carrier 4 until the free receiving rim 71 of the blank 7 can be gripped between the clamping jaws 41, 42 of the carrier head 40 secured on the workpiece carrier 4 (FIG. 6). The action of clamping of the blank 7 at the carrier head 40 of the workpiece carrier 4 completes the transfer of the blank 7 from the transport arm 21 to the workpiece carrier 4. Now, the transport arm 21 moves opposite to the direction of arrow 27 through the transfer opening 8 back into the storage chamber 6, pivots opposite to the direction of arrow 24 into the vertical parallel to the axis of rotation 15 of the receiving carousel 12 and assumes an initial position in the storage chamber 6. Upon pivoting opposite to the direction of arrow 24, the changeover flap 9 closes the transfer opening 8 so that the work chamber 3 is again separated from the storage chamber 6.

In the closed work chamber 3, now processing of the blanks 7 by a milling tool 35 can be performed which is controlled by a milling drive 36.

The frameless blank 7 provided for machining is thus gripped by the transport arm 21 in the storage chamber 6, moved through the transfer opening 8 into the work chamber 3, and transferred to the workpiece holder 4. The frameless blanks 7 is gripped by its receiving rim 71 in the workpiece holder 4 and held at its receiving rim 71 by clamping action in the workpiece holder 4 for processing by milling.

Figure 8:
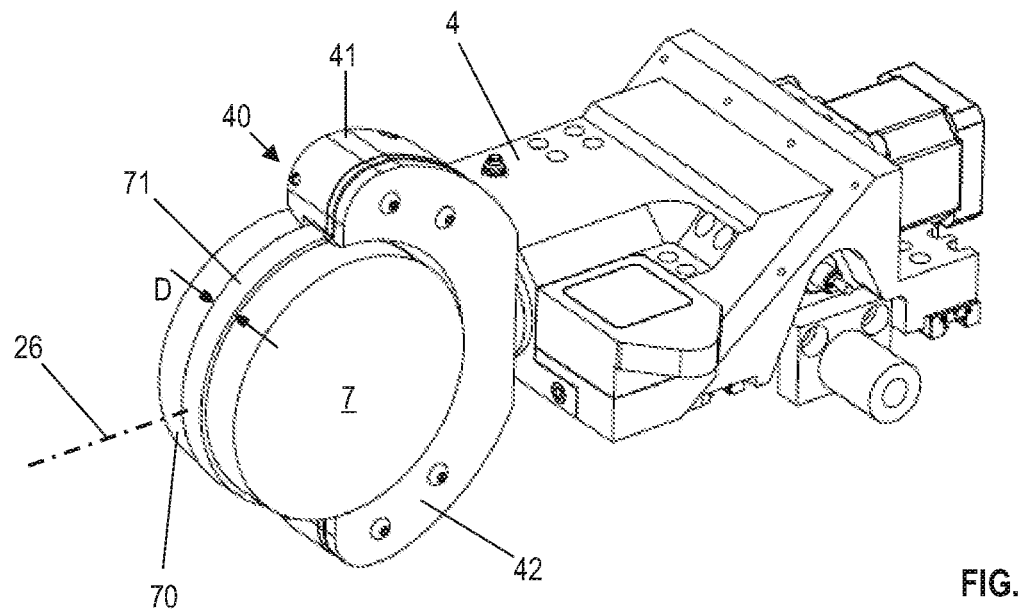
FIG. 8 shows a perspective illustration of the workpiece holder with a frameless blank held by clamping action.

A workpiece carrier 4 is illustrated in perspective illustration in FIG. 8. The carrier head 40 of the workpiece carrier 4 is comprised of two clamping jaws 41, 42 which engage around the outer circumference 70 of a blank 7 to be machined. As illustrated in FIG. 8, the clamping jaws 41, 42 engage the outer circumference 70 of a frameless blank 7 by a circumferential angle of up to 180°.

For its positional change, the carrier head 40 is rotatable in space about an axis of rotation 26 during machining by milling of the frameless blank 7.

Figure 9:
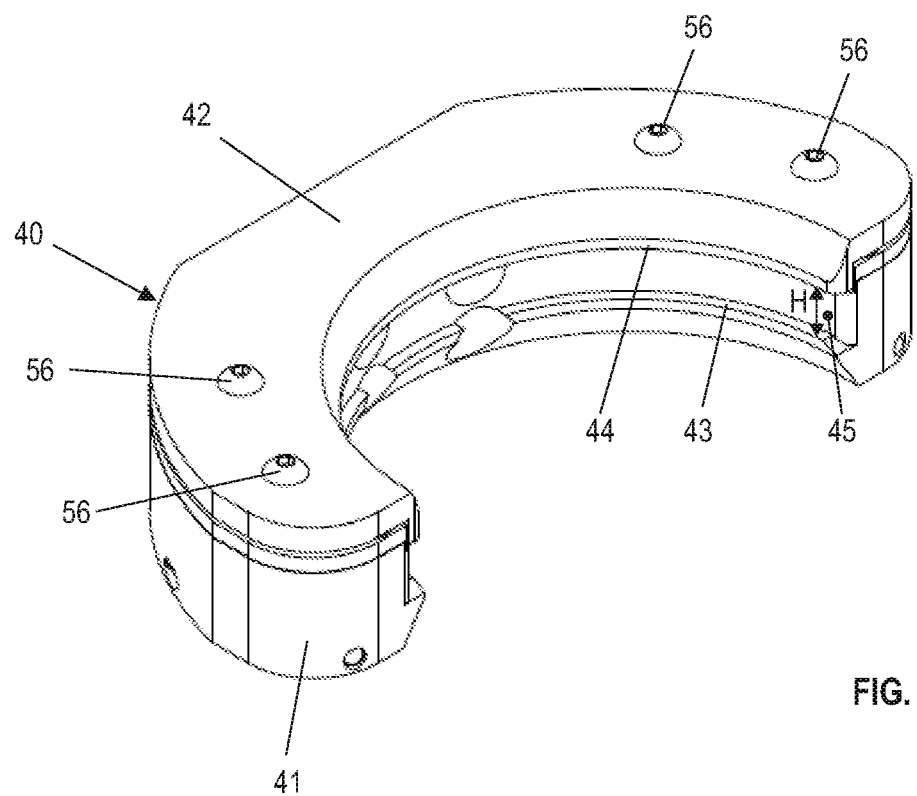
FIG. 9 shows in an enlarged illustration a clamping jaw with a pneumatically actuated clamping claw.
Figure 10:
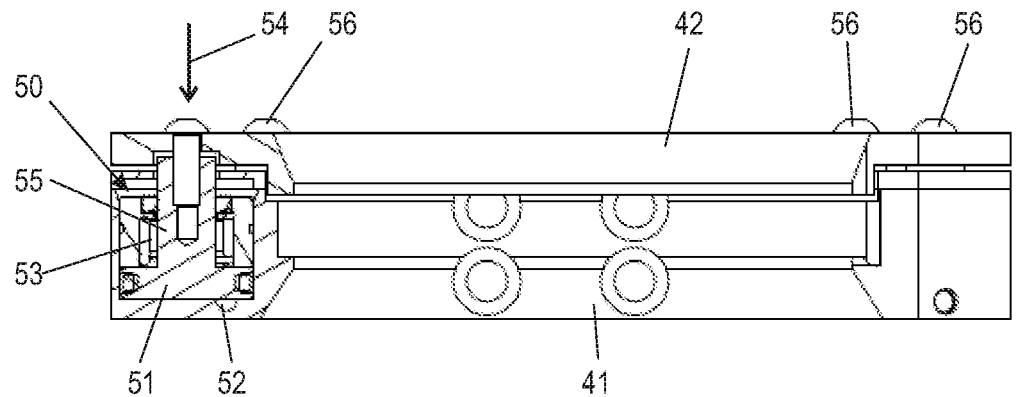
FIG. 10 shows a partial section of the clamping jaw with clamping claw according to FIG. 9.
Figure 11:
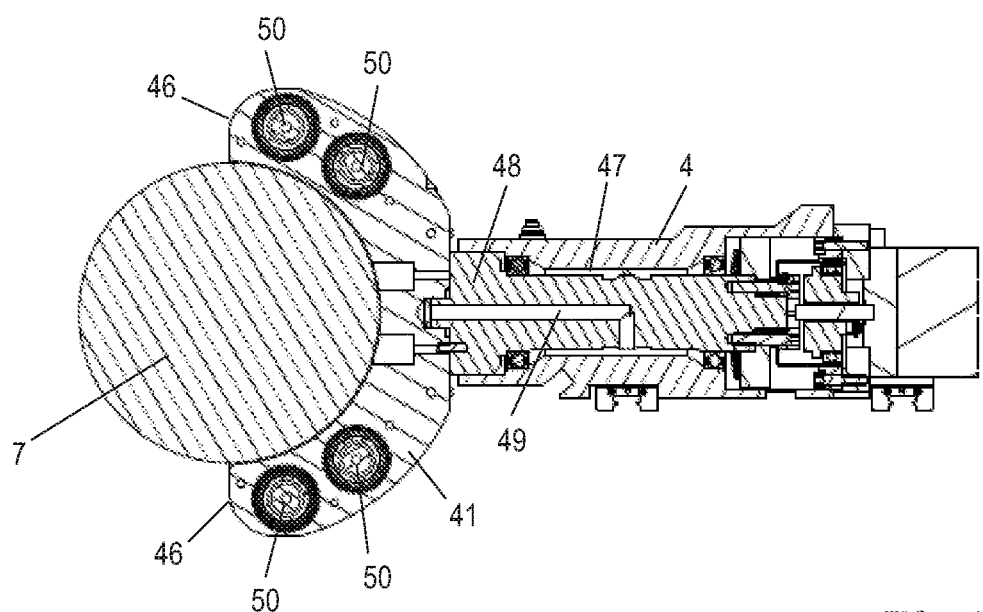
FIG. 11 shows a longitudinal section of the workpiece carrier with pneumatic channels.

The clamping jaws 41 and 42 forming the carrier head 40 are illustrated in FIG. 9 in enlarged view, in FIG. 10 in partial view, and in FIG. 11 in longitudinal section. The clamping jaw 41 is a stationary clamping jaw with a clamping rim 43; the movable clamping jaw 42 is embodied as an adjustable clamping claw 34 with a clamping rim 44. Between the clamping rims 43 and 44 a clamping gap 45 is formed whose minimal height H is smaller than the minimal thickness D of the receiving rim 71 of the blank 7.

Each clamping jaw 41, 42 comprises a semi-circular configuration wherein the stationary clamping jaw 41 is fastened approximately centrally at the end of a shaft 48 of the workpiece carrier 4 (FIG. 11). Between the free ends 46 of the clamping jaws 41 and 42, at least one pneumatic cylinder 50 (FIGS. 10, 11) is acting whose setting piston 51 delimits a pressure chamber 52 in the stationary clamping jaw 41. At the side of the setting piston 51 which is facing away from the pressure chamber 52, a spring 53 is arranged which applies a force to the movable clamping jaw 42, embodied as a clamping claw 34, in clamping direction 54. The spring 53 provides the clamping force of the clamping jaws 41, 42; the spring 53 can be a coil spring, a plate spring or a similar spring element. The piston rod 55 carries the movable clamping jaw 42 embodied as a clamping claw 34; preferably, the clamping jaw 42 is fastened by means of a fastening screw 56 to the free ends of a piston rod 55.

As shown in FIG. 11, between the clamping jaws 41 and 42, a total of four pneumatic cylinders 50 are arranged; two pneumatic cylinders 50 are provided respectively in circumferential direction of the clamping jaws one behind the other in the region of the free ends 46 of the clamping jaws 41, 42.

The compressed air which is required for actuation of the clamping jaw 41 is supplied by a rotary feedthrough 47 that supplies a supply channel 49 in the stationary clamping jaw 42. The supply channel 49 supplies simultaneously compressed air to the pressure chambers of the pneumatic cylinders 50 in order to lift the clamping claw 34 for release of a held blank 7.

The clamping action of the receiving rim 71 of the frameless blanks 7 in the carrier head 40 is realized by spring force of the springs 53 in the pneumatic cylinders 50. The clamping force provided by spring force is canceled by a controlled counterforce which is provided in the embodiment as a pneumatic force acting in the pressure chambers 52.

Figure 12:
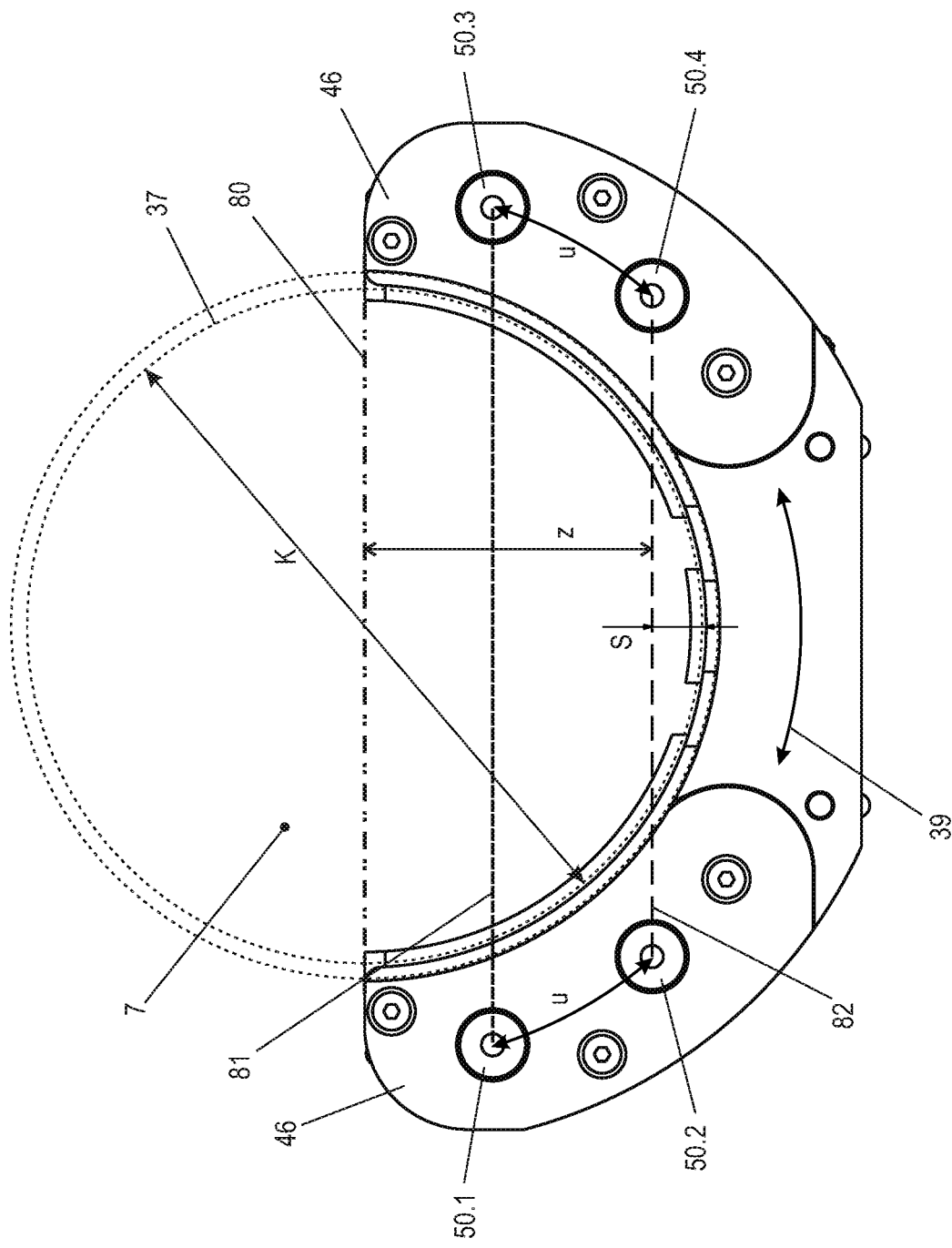
FIG. 12 shows a schematic side view of a clamping jaw for illustrating the position of actuating cylinders.

FIG. 12 shows in detail the position of the actuating cylinders 50.1, 50.2, 50.3, 50.4, embodied as pneumatic cylinders 50, of the clamping jaws 40, 41 of the workpiece holder 4. In the region of the free ends 46 of the approximately semicircular clamping jaws 41, 42 an actuating cylinder 50.1 and 50.3 is provided, respectively. The actuating cylinders 50.2 and 50.4 which are moreover provided between the stationary clamping jaw 41 and the movable clamping jaw 42 are positioned in circumferential direction 39 at a circumferential spacing u relative to the neighboring actuating cylinders 50.1 and 50.3, respectively. The arrangement of the actuating cylinders 50.1, 50.2, 50.3, 50.4 is provided such that a straight connecting line 81 between the actuating cylinders 50.1 and 50.3 is positioned parallel to the connecting line 80 between the free ends 46 of the clamping jaws 41, 42. The connecting line 80 corresponds advantageously to a central diameter of the blank 7 to be held with a diameter K which is illustrated in FIG. 12 in dotted line.

A connecting line 82 between the further actuating cylinders 50.2 and 50.4 which are positioned at a circumferential spacing u relative to the actuating cylinder 50.1 and 50.3 is advantageously parallel to the connecting line 81 of the free ends 46 arranged at the actuating cylinders 50.1 and 50.3. The connecting line 82 is positioned parallel to the connecting line 80 which advantageously corresponds to the central diameter of the blank 7. The spacing z of the connecting line 82 to the connecting line 80 is to be configured at specified value. The position of the connecting line 82 of the inner actuating cylinders 50.2 and 50.4 is to be provided such that the connecting line 82 forms maximally a tangent to the outer circle diameter 37 of the blank 7. In particular, the connecting line 82 forms a chord to the circle diameter of the blank 7. In this context, a spacing S between the connecting line 82 shown as a chord and the circle diameter 37 is provided which is in particular between 5 and 10 mm.

Figure 13:
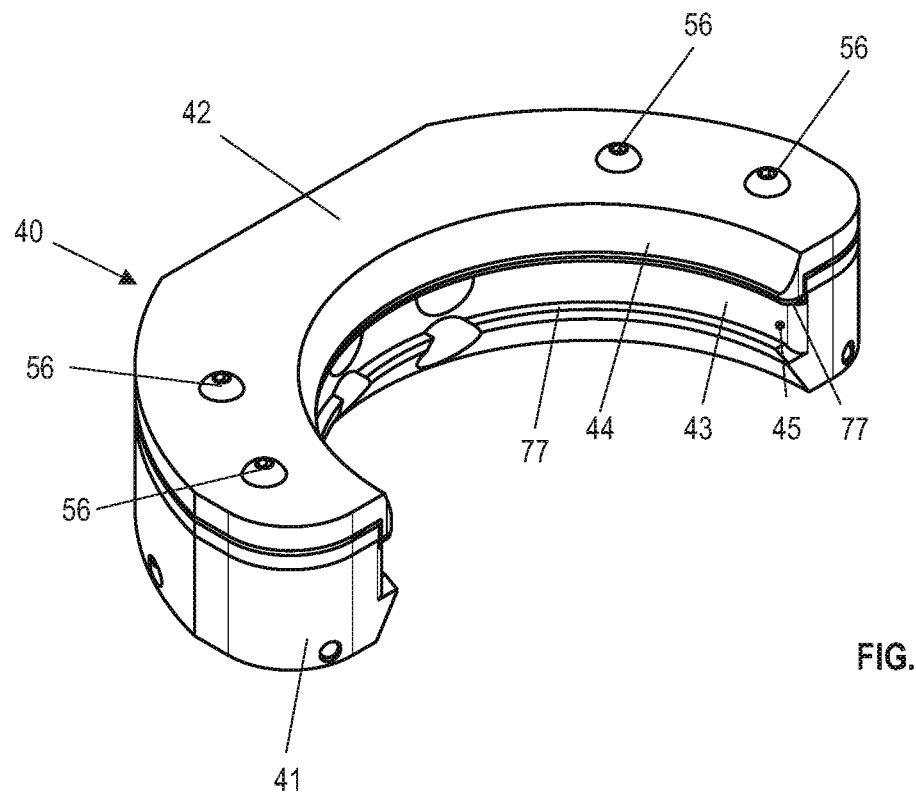
FIG. 13 shows a perspective illustration of a clamping jaw with a rubberized clamping claw.

In a further embodiment of the invention according to FIG. 13, the clamping rim 44 of the movable clamping jaw 42 forming a clamping claw 34 and/or the clamping rim 43 of the stationary clamping jaw 41 can be embodied to be resilient. A resilient configuration of the clamping surface of the clamping rim 43, 44 can be achieved by a rubber structure 38. Such a rubber structure 38 can be formed as a glued-on rubber mat, as a vulcanized-on rubber, as an extruded-on polyurethane bead or the like. The rubber structure can compensate small thickness tolerances and unevenness at the workpiece surface. The effective clamping surface between the clamping rims 43 and 44 is maximized and the friction between the receiving rim 71 of the workpiece and the clamping jaws 41, 42 is increased.

Figure 14:
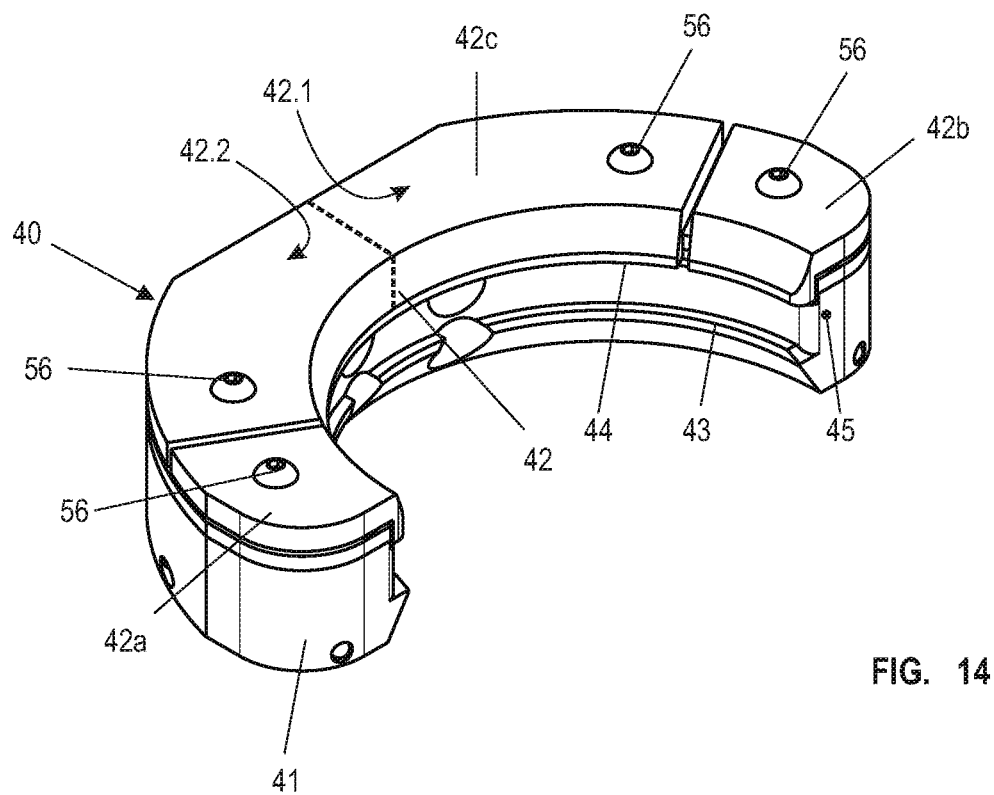
FIG. 14 shows a perspective illustration of a clamping jaw with a divided clamping claw.

In the embodiments of FIGS. 8 through 13, there is only one movable clamping jaw 42 provided at which all actuating cylinders 50.1, 50.2, 50.3, 50.4 arranged within the workpiece holder 4 are engaging, while FIG. 14 shows a division of the clamping jaw 42 into several clamping jaw sections. In a first embodiment, the clamping jaw 42 could be divided at the center, as illustrated in dashed line in FIG. 14. Two actuating cylinders 50.1, 50.2 and 50.3, 50.4, respectively, engage a respective clamping jaw section 42.1 and 42.2.

Alternatively, an embodiment is also advantageous wherein each one of the actuating cylinders 50.1, 50.2, 50.3, 50.4 engages a separate clamping jaw section 42a, 42b, 42c for which purpose the clamping jaw section 42c may be divided at the dashed line. Expediently, the central clamping jaw section 42c is moved by two actuating cylinders 50.2, 50.4. The correlation of one respective actuating cylinder 50.1, 50.2, 50.3, 50.4 to one respective clamping jaw section ensures that the actuating cylinders 50.1, 50.2, 50.3, 50.4 are mechanically independent from each other and cannot mutually lock or jam each other. A piston rod 55 of an actuating cylinder 50.1, 50.2, 50.3, 50.4 takes over the axial force transmission and advantageously also the transmission of a moment onto the workpiece. The guiding action of the piston and of the piston rod is accordingly of a stiff construction.

Figure 15:
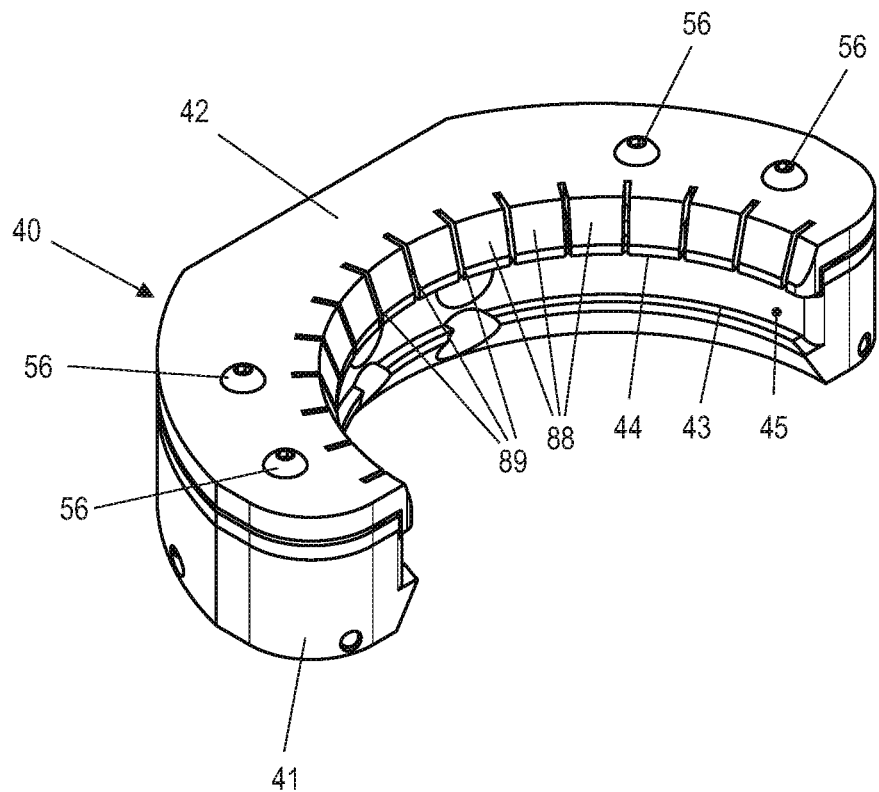
FIG. 15 shows a perspective illustration of a clamping jaw with a clamping claw formed of a plurality of spring elements.
Figure 16:
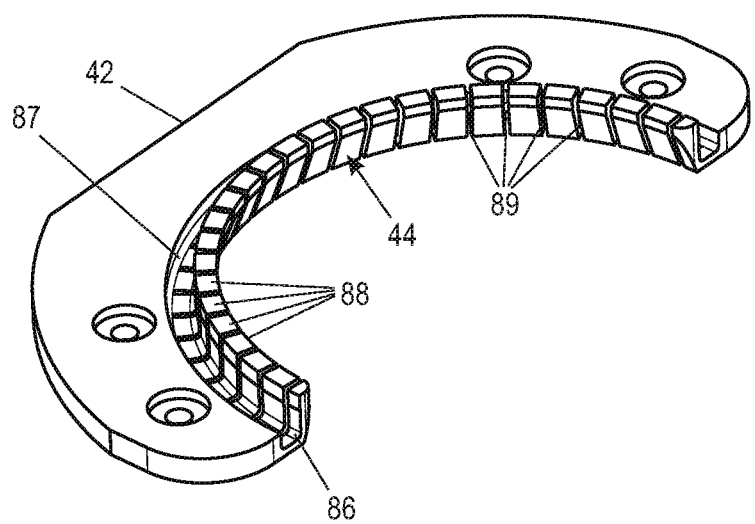
FIG. 16 shows a perspective illustration of a clamping claw comprised of a plurality of spring elements.

In the embodiment according to FIGS. 15 and 16, the movable clamping jaw 42 is of a one-piece configuration and is comprised of a plurality of spring elements 88. Expediently, the movable clamping jaw 42 forming a clamping claw 34 is comprised of spring steel and is in particular of a one-piece configuration. The individual spring elements 88 are produced by introducing separating slots 89 wherein the separating slots 89 are introduced approximately radially into the clamping rim 44 of the movable semi-circular clamping jaw 42. Behind the clamping rim 44 which forms a pressure surface, a part-circular groove 87 is provided by milling in order to reduce the cross-section of the spring elements 88 and to improve in this way the spring property. In order to minimize the notch effect for the clamping force transmission, it is provided to round the inner edges 86.

Upon clamping a blank 7, each spring element 88 can adapt to possible imprecisions of the workpiece so that a good clamping action is achieved. Due to the cross-sectional weakening by means of the circumferentially extending groove 87, the individual spring elements 88 are yielding and slightly springy. By means of the selected magnitude of the cross-sectional weakening, the number of introduced separating slots 89 or the number of formed spring elements 88 and/or their width as well as the selected material for the clamping jaw 42, the hardness or softness of the clamping claw 34 can be adjusted.

In FIGS. 17 to 20, an idle receptacle 10 for blanks 7 is illustrated in detail. Each idle receptacle is comprised of a support base 16 which is configured to match the design of the T-groove in the carousel plate 13. A U-shaped semi-circular frame 90 is secured on the support base 16 and is connected fixedly to the support base 16. A leg 91 of the frame 90 can be pivoted relative to the frame 90 so that the U-shaped idle receptacle 10 can be opened at one side. The movable leg 91 is pivotably connected in the region of the base stay 92 of the idle receptacle 10, preferably by pivot bolts 93. The leg 91 is force-loaded by a spring 94 wherein the spring 94 is arranged such that in open position of the leg 91 the spring force secures stably the leg 91 in the open position. When the resilient leg 91 is pivoted into its closing position, the spring force secures the leg 91 stably in the closing position.

For inserting a blank 7 into the idle receptacle 10, the leg 91 is folded downwardly so that the opening of the idle receptacle 10 for insertion of the blank 7 is greater, whereby handling is simplified. The leg 91 is moved about the pivot bolts 93 that define a fixed axis of rotation and can be pivoted by 90° or more forwardly and downwardly. The movement of the leg 91 is controlled by the spring 94 which is embodied as a tension spring. In the closed end position of the leg 91, the opening of the idle receptacle 10 is minimally smaller than the diameter d of a blank 7. The leg 91 exerts on a blank 7 inserted into the idle receptacle 10 a minimal radial spring force so that the blank 7 is safely held in the idle receptacle 10. Diameter tolerances of different blanks 7 can be compensated also by the spring-loaded leg 91.

Figure 17:
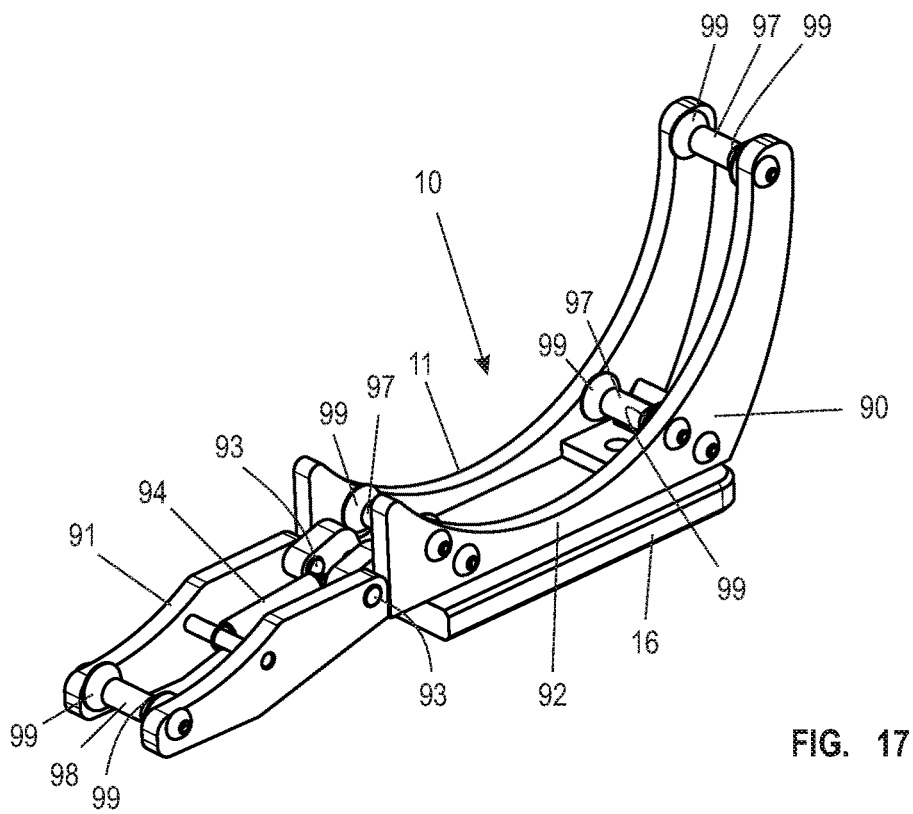
FIG. 17 shows a perspective illustration of an open idle receptacle for loading a blank.
Figure 18:
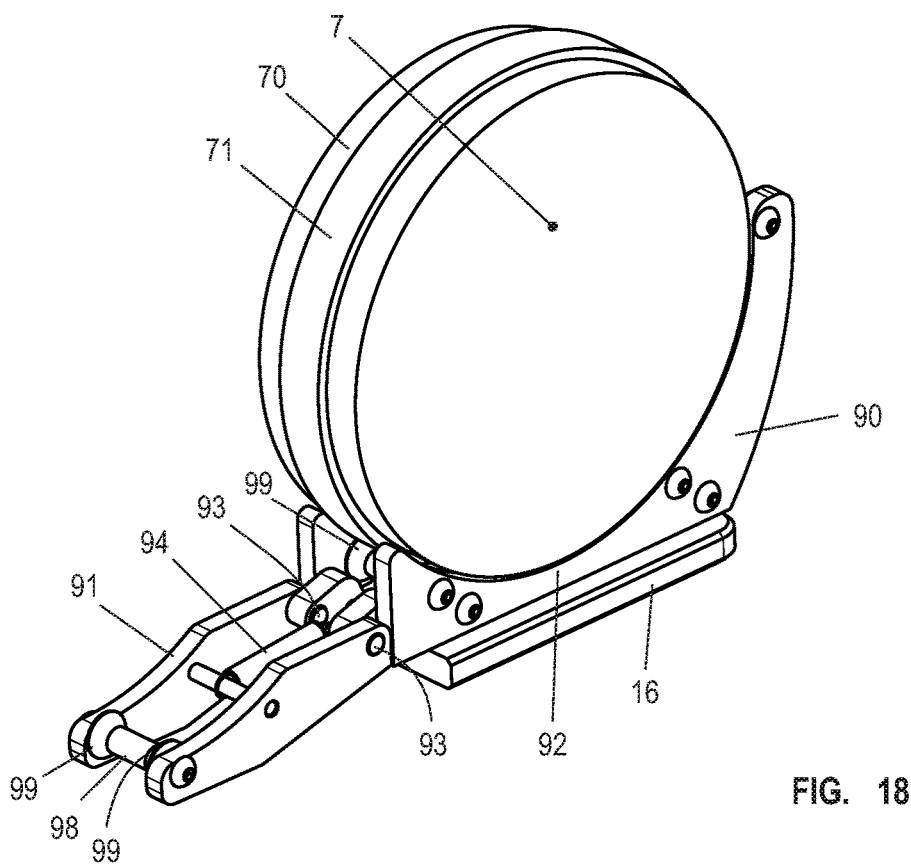
FIG. 18 shows a perspective illustration of an open idle receptacle according to FIG. 17 with an inserted blank.
Figure 19:
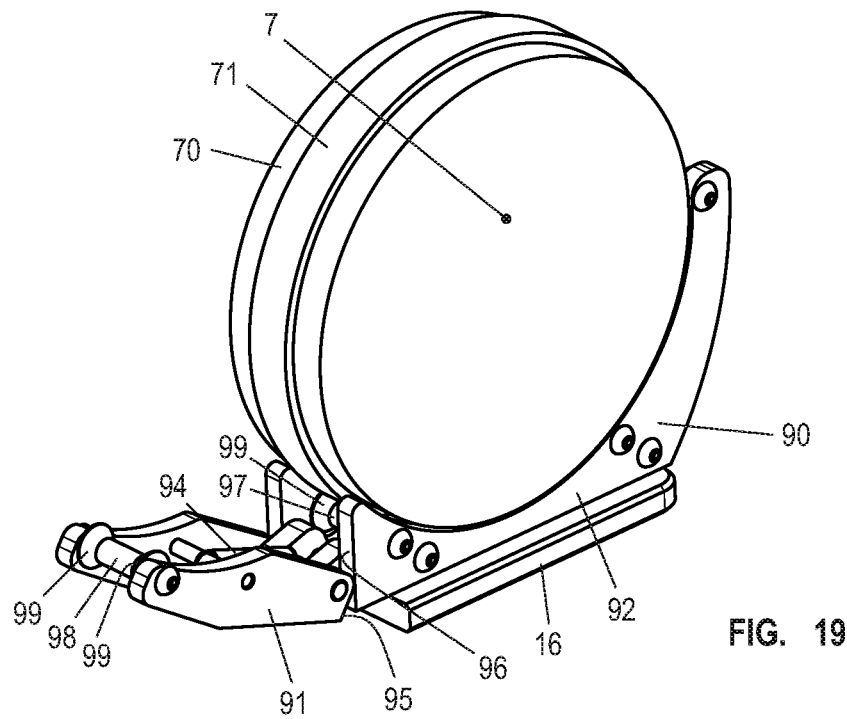
FIG. 19 shows a perspective illustration of a partially closed idle receptacle with an inserted blank according to FIG. 18.
Figure 20:
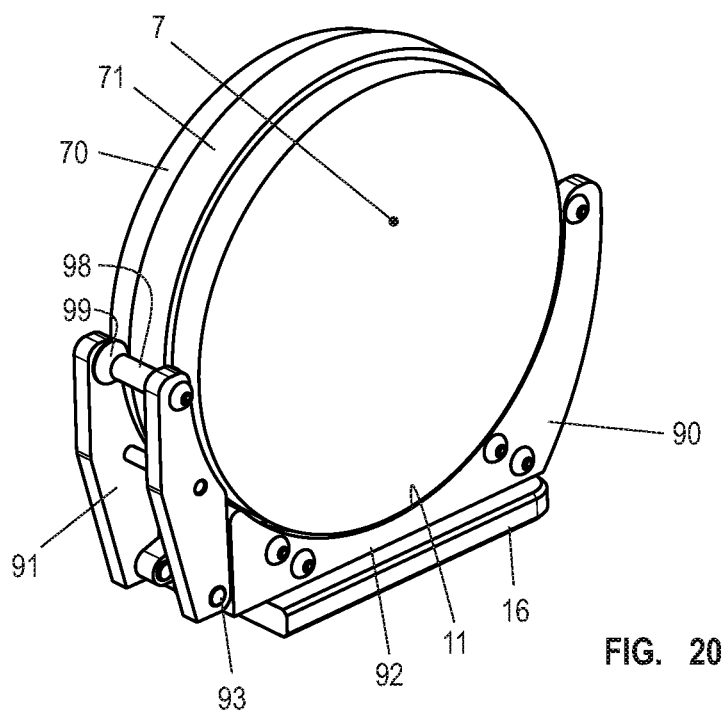
FIG. 20 shows a perspective illustration of a closed idle receptacle with inserted blank.

When opening the idle receptacle 10 by pivoting the leg 91 into its lower end position (FIGS. 17, 18), the spring 94—like an elbow lever—will move past a stretched position with a dead center. After having moved past the stretched position, the leg 91 is secured in the lower end position by the spring 94 and does not snap upwardly in an uncontrolled fashion. Stop edges 95 in the base area of the leg 91 and stop edges 96 at the base stay 92 of the frame 90 delimit the rotational movement of the leg 91 and define its stable open position (FIG. 17).

The blank 7 itself is resting only against four contact points 97, 98 in the idle receptacle 10. The frame 90 comprises three fixed contact points 97; a movable contact point 98 is provided at the leg 91. The spring force of the leg 91 which is acting in the closing position of the idle receptacle 10 (FIG. 20) pushes the blank 7 against the three fixed contact points 97 of the frame 90.

Advantageously, the four contact points 97, 98 are designed such that they form in particular a linear contact or advantageously a small areal contact relative to the blank 7.

In order to secure the axial position of the blank 7 in the idle receptacle 10, the contact points 97, 98 are formed with lateral bevels 99, preferably at an angle of 30° to 45°. The positionally precise insertion of blanks 7 is facilitated for the operator. Also, returning a blank 7 by the transport arm 21 is possible in a simpler and safer way by the configuration of the contact points 97, 98. The positionally precise placement of the blank 7 into the idle receptacle 10 is ensured. The bevels 99 form insertion aids and position the blank 7 almost automatically.

In FIGS. 21 to 26, a further embodiment of a carrier head 40 with clamping jaws 41, 42 is shown. The basic configuration is similar to the embodiments of the carrier heads 40 according to FIGS. 9 to 16 so that same reference characters are used for same parts.

Figure 21:
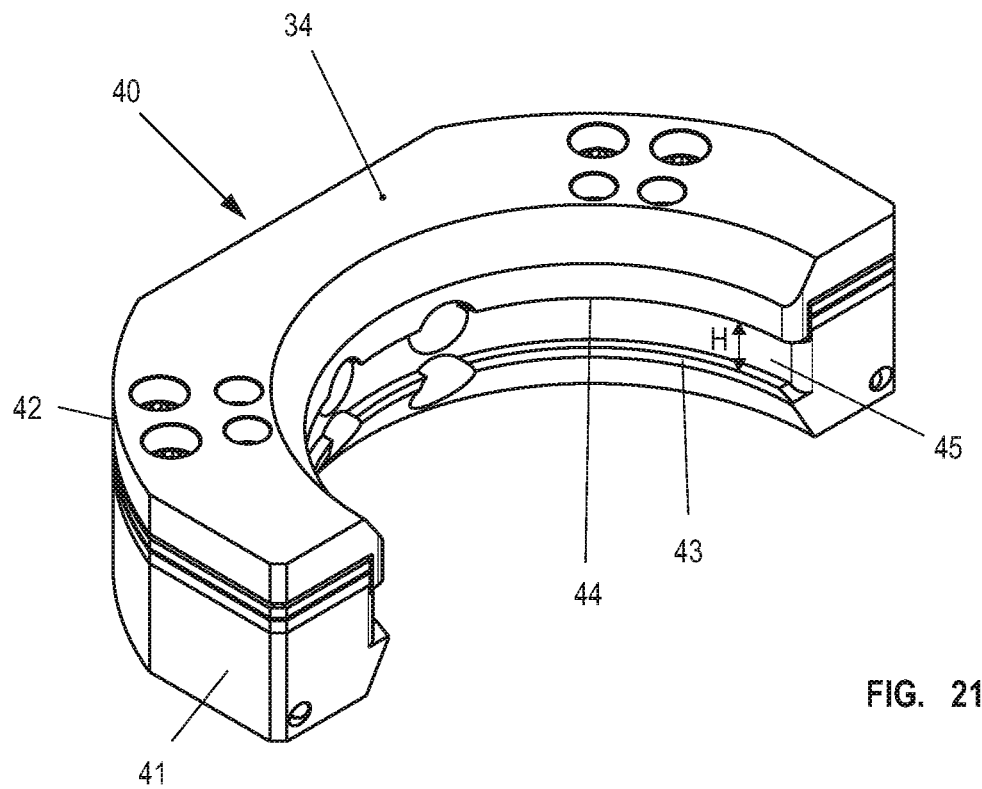
FIG. 21 shows a perspective illustration of a further embodiment of a carrier head of a clamping jaw with a clamping claw.
Figure 22:
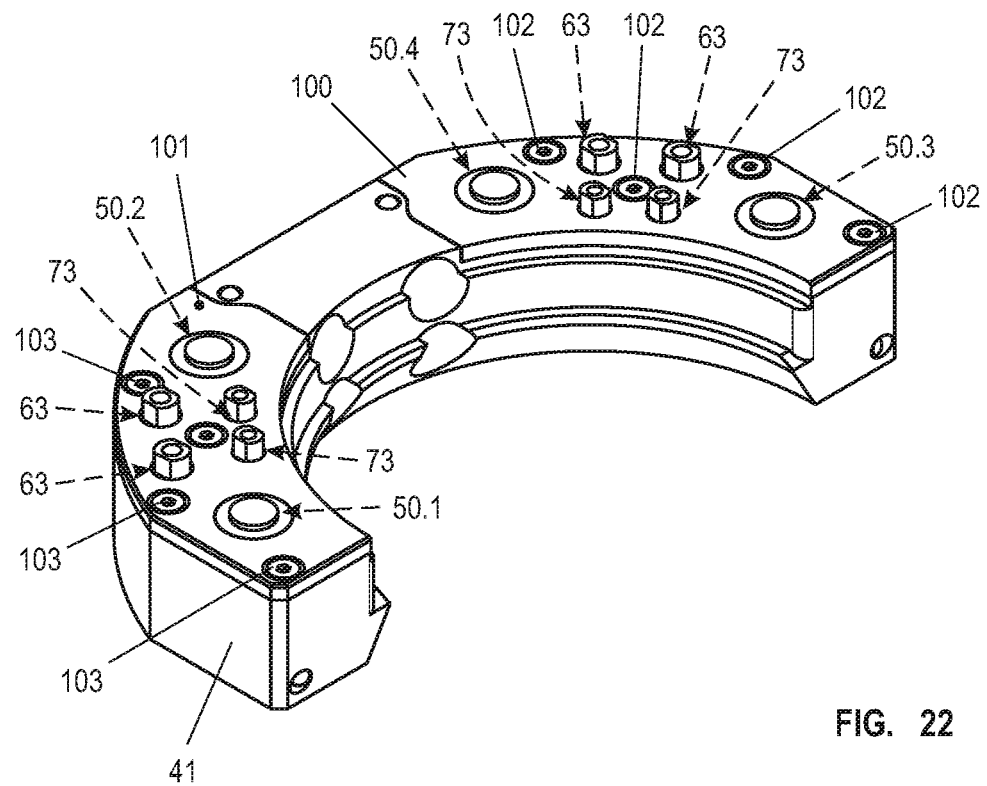
FIG. 22 shows a perspective illustration of the stationary clamping jaw of the carrier head according to FIG. 21 after demounting the clamping claw.
Figure 23:
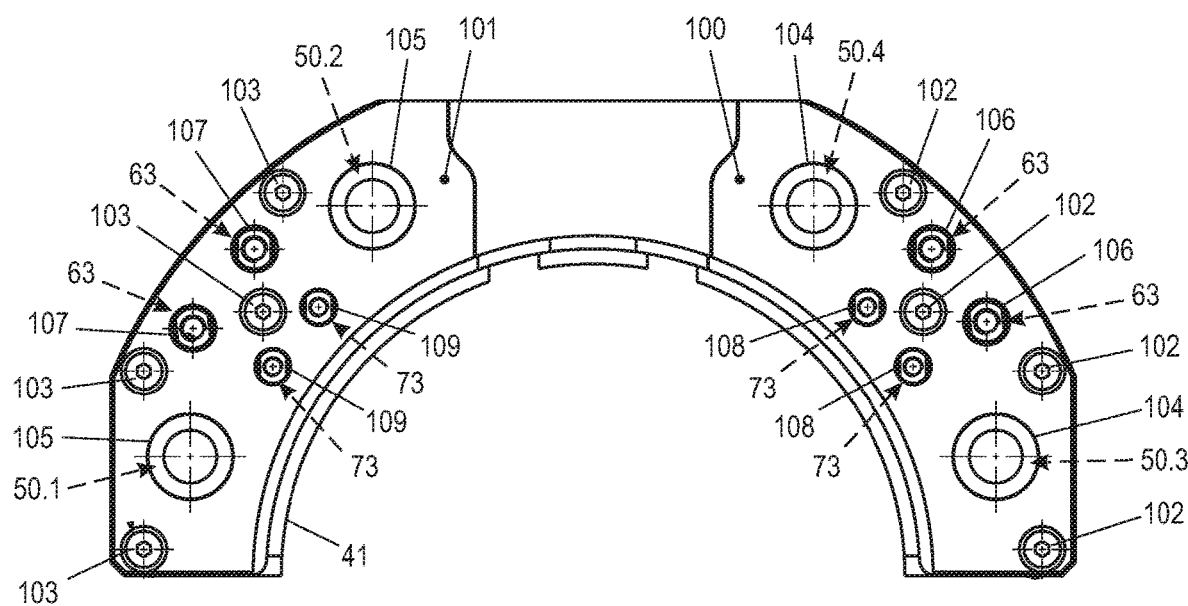
FIG. 23 shows a plan view of the stationary clamping jaw according to FIG. 22 after demounting the clamping claw.
Figure 24:
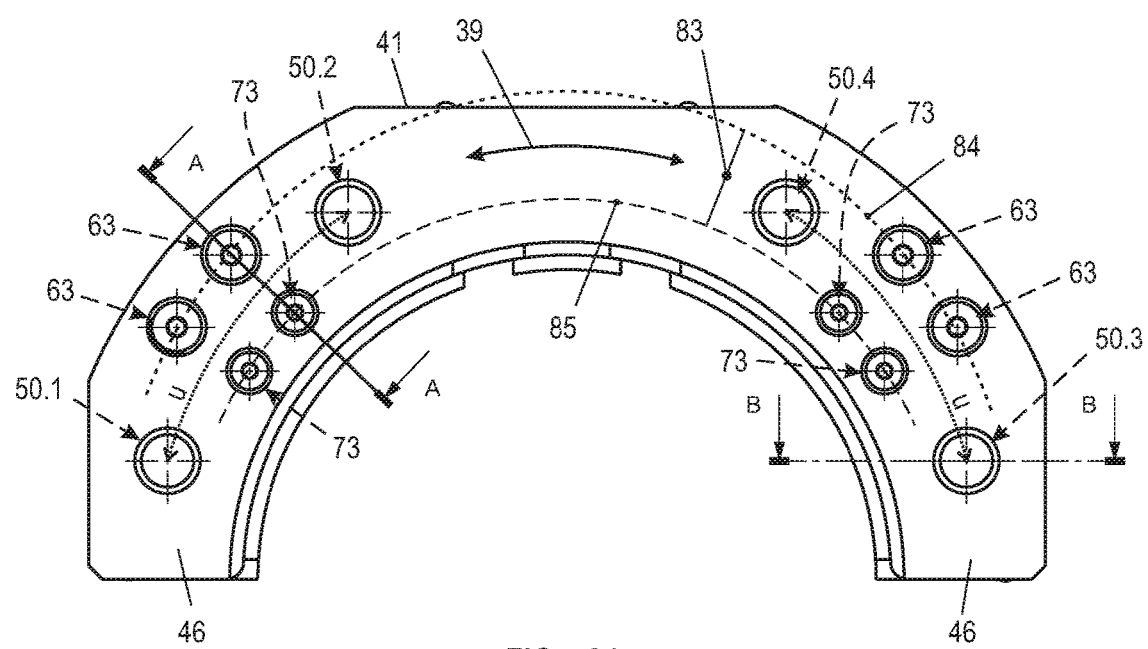
FIG. 24 shows a schematic plan view of the stationary clamping jaw according to FIG. 23.
Figure 25:
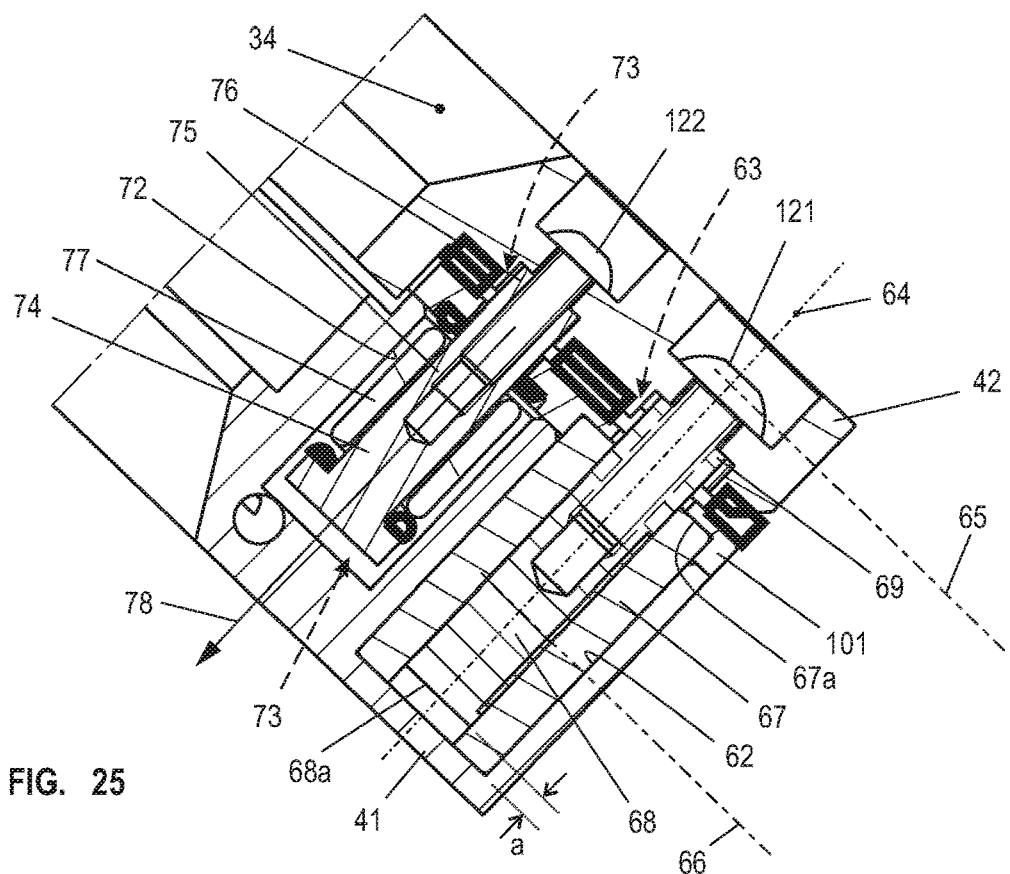
FIG. 25 shows a section along the line A-A in FIG. 24 through a mechanical guiding element and a force storage device of the stationary clamping jaw.
Figure 26:
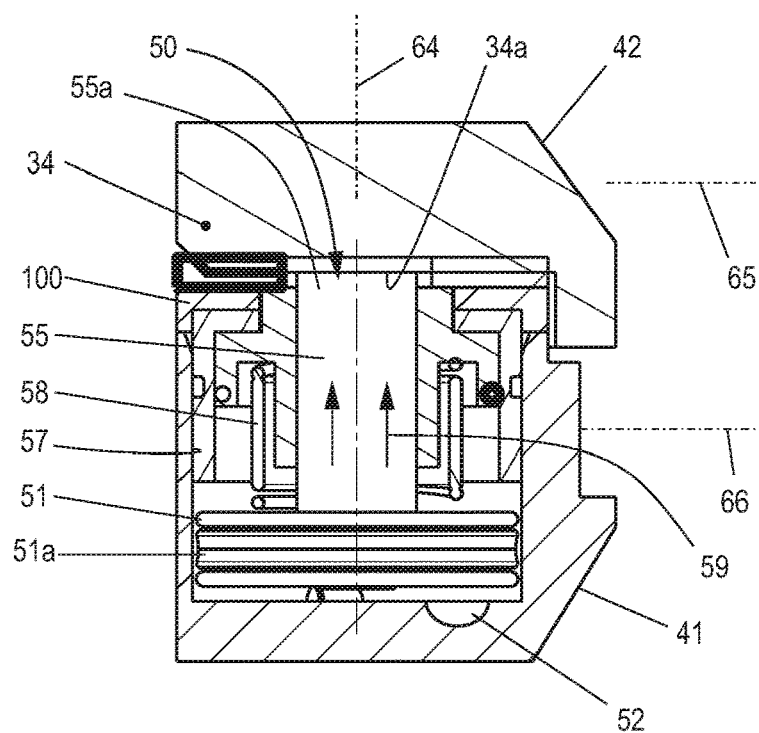
FIG. 26 shows a section along the line B-B in FIG. 24 through an actuating cylinder embodied as a pneumatic cylinder.

In the embodiment according to FIGS. 21 to 26, the carrier head 40 is comprised of a stationary clamping jaw 41 and a movable clamping jaw 42 which is also referred to as clamping claw 34 (FIG. 21). The actuation of the clamping claw 34 relative to the stationary clamping jaw 41 is realized by actuating cylinders 50.1, 50.2, 50.3, 50.4 embodied as pneumatic cylinders 50 (FIG. 22) as they are also shown in the embodiment according to FIGS. 10 through 12. The pneumatic cylinders 50 embodied as actuating cylinders 50.1, 50.2, 50.3, 50.4 are only resting with the piston rod 55 of the setting piston 51 against the clamping claw 34, as illustrated in FIG. 26. The free end of the piston rod 55 has no fixed connection with the clamping claw 34. The in particular single-action setting piston 51 forces the clamping claw 34 only pneumatically in the direction of arrow 59 (FIG. 26) in upward direction. The return of the setting piston 51 is realized by a restoring spring 58 which is preferably arranged in the pneumatic cylinder 50. The restoring spring 58 is expediently a coil spring surrounding the piston rod 55.

Adjacent to the actuating cylinders 50.1, 50.2, 50.3, 50.4 embodied as pneumatic cylinders 50 and preferably serving only for opening the clamping claw 34, mechanical guiding element 63 that are embodied as straight guiding devices are provided between the stationary clamping jaw 41 and the movable clamping jaw 42 forming the clamping claw 34. By means of the straight guiding devices, the clamping claw 34 is moveable against the stationary clamping jaw 41 along a straight line 64 (FIG. 25). The straight line 64 is in particular perpendicular to the plane 65 formed by the movable clamping jaw 42 as well as perpendicular to the plane 66 determined by the stationary clamping jaw 41. The guiding element 63 is formed in particular by a recirculating ball bushing 67 with an axially movable guide shaft 68 by means of which the clamping claw 34 is guided in the direction of the straight line 64. The guide shaft 68 is connected with its free end 69 to the clamping claw 34, in particular screwed by a fastening screw 121 to the clamping claw 34. The guide shaft 68 which is in particular axially guided in the recirculating ball bushing 67 not only provides for guiding of the clamping claw 34 relative to the stationary clamping jaw 41 but moreover can also absorb the moments that occur during clamping.

In addition to the actuating cylinders 50.1, 50.2, 50.3, 50.4 which are embodied as pneumatic cylinders 50 and to the mechanical guiding elements 63, force storage devices 73 are moreover provided. A force storage device 73 is comprised substantially of an in particular non-guided piston 74 (FIG. 25) with a pull rod 75 whose free end 76 is connected, in particular screwed by a fastening screw 122, with the movable clamping jaw 42 forming the clamping claw 34. The piston 74 is loaded by an adjusting spring 77 which provides the clamping force for the clamping claw 34. The adjusting spring 77 is supported at the stationary clamping jaw 41, in particular at a cover 101 of the stationary clamping jaw 41 and forces the piston 74 with a predetermined spring force in the direction of arrow 78 in the direction toward the stationary clamping jaw 41. The adjusting spring 77 of the force storage device 73 pulls the clamping claw 34 in downward direction against the stationary clamping jaw 41. By means of the spring force of the adjusting spring 77, the blank clamping action is realized.

The pneumatic cylinder 50, the mechanical guiding element 63, and the force storage device 73 are received in receptacles of the stationary clamping jaw 41. A first cylinder bore 57 (FIG. 26) is provided for the pneumatic cylinder 50 as a receptacle, a second cylinder bore 62 (FIG. 25) is provided for the guiding element 63, and a third cylinder bore 72 (FIG. 25) is provided for the force storage device 73. The cylinder bores 57, 63, 73 are blind bores and are machined from the direction of the movable clamping jaw 42 into the stationary clamping jaw 41. The axes of the blind bores are positioned parallel to each other and relative to the straight line 64 of the mechanical guiding element 63 which forms a straight guiding action.

In the illustrated embodiment according to FIGS. 21 to 24, the position of the actuating cylinders 50.1, 50.2, 50.3, 50.4, embodied as pneumatic cylinders 50, of the guiding elements 63, and of the force storage devices 73 of the carrier head 40 of the workpiece holder is illustrated in detail. The arrangement corresponds preferably to that described in FIG. 12. In the region of the free ends 46 of the approximately semi-circular clamping jaws 41, 42, an actuating cylinder 50.1 and 50.3 is provided, respectively. The actuating cylinders 50.2 and 50.4 which are furthermore positioned between the stationary clamping jaw 41 and the movable clamping jaw 42 are displaced in circumferential direction 39 at a circumferential spacing u relative to the neighboring actuating cylinders 50.1 or 50.3, respectively. The arrangement corresponds preferably to that of FIG. 12 with the spacings and connecting lines indicated therein.

In the illustrated embodiment according to FIGS. 21 to 24, each actuating cylinder 50.1, 50.2, 50.3, 50.4 has correlated therewith at least one guiding element 63 and one force storage device 73. As shown in particular in FIGS. 23 and 24, at least one guiding element 63 and one force storage device 73 are positioned within the circumferential spacing u between two actuating cylinders 50.1 and 50.2 or two actuating cylinders 50.3 and 50.4; in the embodiment, two guiding elements 63 and two force storage devices 73 are positioned within the circumferential spacing u between two actuating cylinders 50.1 and 50.2 or 50.3 and 50.4.

The preferred embodiment comprises thus four actuating cylinders 50.1, 50.2, 50.3, 50.4 embodied as pneumatic cylinders 50, four guiding elements 63 as linear guides, and four force storage devices 73 for providing the clamping force.

The guiding elements 63, in particular all guiding elements 63 of the tool holder, are positioned on a common circular arc 84 which is close to the outer rim of the clamping jaws 41, 42. The force storage devices 73, in particular all force storage devices 73, are positioned on a common circular arc 85 which is farther removed from the outer rim of the clamping jaws 41, 42 than the circular arc 84. The actuating cylinders 50.1, 50.2, 50.3, and 50.4 are positioned in the annular section 83 which is formed between the circular arcs 84 and 85.

The cylinder bores 57 of the actuating cylinders 50.1 and 50.2 as well as the cylinder bores 62 of the guiding elements 63 arranged between them, and the cylinder bores 72 of the force storage devices 73 arranged between them are closed off by a common cover 101 which is fastened by fastening screws 103 to the stationary clamping element 41. In the cover 101, through openings 105, 107 and 109 for the free end of the setting piston 51, the free end 69 of the guide shaft 68 as well as the free end 76 of the pull rod 75 of the force storage device 73 are provided.

Correspondingly, the cylinder bores 57 of the actuating cylinders 50.3 and 50.4 as well as the cylinder bores 62 of the guiding elements 63 arranged between them, and the cylinder bores 72 of the force storage devices 73 arranged between them are closed off by a common cover 100 which is secured by fastening screws 102 to the stationary clamping element 41. In the cover 100, through openings 104, 106, and 108 for the free end of the setting piston 51, the free end 69 of the guide shaft 68 as well as the free end 76 of the pull rod 75 of the force storage device 73 are provided.

In FIG. 25, the guiding element 63 and the force storage device 73 are illustrated in section. The recirculating ball bushing 67 is inserted into the cylinder bore 62, in particular without clearance. The recirculating ball bushing 67 is seated with an end face on the bottom of the blind bore. The other end face 67a of the recirculating ball bushing 67 is resting against the screwed-on housing cover 100 or 101. The recirculating ball bushing 67 is secured axially without clearance between the bottom of the blind bore and the cover 100, 101.

The guide shaft 68 is axially inserted into the recirculating ball bushing 67. The guide shaft 68 is axially movably held in the recirculating ball bushing 67 and preferably guided without clearance. Between the bottom of the blind bore and the inner end 68a of the guide shaft 68, axial play a is provided.

The force storage device 73 is comprised of the pull rod 75 whose upper end 76 is screw-connected to the clamping claw 24. The lower end of the pull rod 75 comprises an annular plate as a support for the adjusting spring 77. The adjusting spring 77 acts between the annular plate of the pull rod 75 and the cover 100, 101 which closes off the cylinder bore 72 of the force storage device 73.

FIG. 26 shows in section a pneumatic cylinder 50. The actuating cylinders 50.1, 50.2, 50.3, 50.4 are embodied in accordance with the illustration of the pneumatic cylinder 50.

The cylinder bore 57 comprises the pressure chamber 52 delimited by the bottom of the blind bore and the setting piston 51. For sealing the pressure chamber 52, the setting piston 51 supports a piston seal 51a. The piston rod 55 is only resting with its end 55a against the contact surface 34a of the clamping claw 34. The restoring spring 58 is arranged between the setting piston 51 and the cover 100, 101 of the clamping jaw 41. The restoring spring 58 restores the setting piston 51 only into its initial position. Since the end 55a of the setting piston 51 is only resting against the clamping claw 34, the arrangement provides a unidirectionally acting pneumatic cylinder 50. The setting piston 51 exerts an opening force on the clamping claw 34 exclusively in the direction of arrow 59.

What is claimed is:
1. A dental milling machine comprising:
   a storage chamber;
   idle receptacles arranged in the storage chamber and configured to store a plurality of blanks, wherein the plurality of blanks each are placed without frame as a frameless blank into the idle receptacles;
   a transfer device arranged in the storage chamber and comprising a transport arm;
   a work chamber adjoining the storage chamber;
   a transfer opening arranged between the work chamber and the storage chamber;
   wherein the transport arm is configured to grip a frameless blank stored in one of the idle receptacles in the storage chamber and to move the frameless blank through the transfer opening into the work chamber;
   a workpiece holder arranged in the work chamber and configured to receive the frameless blank from the transport arm, wherein the workpiece holder is configured to grip the frameless blank by a receiving rim of the frameless blank, and wherein the workpiece holder, for milling the frameless blank in the work chamber by a milling tool, is configured to hold by a clamping action the frameless blank at the receiving rim;
   a housing enclosing the work chamber and the storage chamber;
   a bottom disposed in the housing, wherein the bottom separates the work chamber from the storage chamber, and wherein the transfer opening is disposed in the bottom.

2. The dental milling machine according to claim 1, wherein the storage chamber is positioned below the work chamber.

3. The dental milling machine according to claim 1, further comprising a receiving carousel arranged in the storage chamber and comprising a carousel plate, wherein the idle receptacles are arranged on the carousel plate of the receiving carousel.

4. The dental milling machine according to claim 3, wherein the receiving carousel rotates about a vertical axis of rotation.

5. A dental milling machine comprising:
   a storage chamber;
   idle receptacles arranged in the storage chamber and configured to store a plurality of blanks, wherein the plurality of blanks each are placed without frame as a frameless blank into the idle receptacles;
   a transfer device arranged in the storage chamber and comprising a transport arm;
   a work chamber adjoining the storage chamber;
   a transfer opening arranged between the work chamber and the storage chamber;
   wherein the transport arm is configured to grip a frameless blank stored in one of the idle receptacles in the storage chamber and to move the frameless blank through the transfer opening into the work chamber;
   a workpiece holder arranged in the work chamber and configured to receive the frameless blank from the transport arm, wherein the workpiece holder is configured to grip the frameless blank by a receiving rim of the frameless blank, and wherein the workpiece holder, for milling the frameless blank in the work chamber by a milling tool, is configured to hold by a clamping action the frameless blank at the receiving rim;
   wherein the idle receptacles each are embodied as a semi-circular receiving shell and configured for upright reception of the frameless blanks.

6. A dental milling machine comprising:
   a storage chamber;

idle receptacles arranged in the storage chamber and configured to store a plurality of blanks, wherein the plurality of blanks each are placed without frame as a frameless blank into the idle receptacles;
a transfer device arranged in the storage chamber and comprising a transport arm;
a work chamber adjoining the storage chamber;
a transfer opening arranged between the work chamber and the storage chamber;
wherein the transport arm is configured to grip a frameless blank stored in one of the idle receptacles in the storage chamber and to move the frameless blank through the transfer opening into the work chamber;
a workpiece holder arranged in the work chamber and configured to receive the frameless blank from the transport arm, wherein the workpiece holder is configured to grip the frameless blank by a receiving rim of the frameless blank, and wherein the workpiece holder, for milling the frameless blank in the work chamber by a milling tool, is configured to hold by a clamping action the frameless blank at the receiving rim;
wherein the idle receptacles each are embodied as a U-shaped frame with a pivotable leg.

7. The dental milling machine according to claim 1, wherein the transport arm is configured to grip the receiving rim of the frameless blank.

8. A dental milling machine comprising:
a storage chamber;
idle receptacles arranged in the storage chamber and configured to store a plurality of blanks, wherein the plurality of blanks each are placed without frame as a frameless blank into the idle receptacles;
a transfer device arranged in the storage chamber and comprising a transport arm;
a work chamber adjoining the storage chamber;
a transfer opening arranged between the work chamber and the storage chamber;
wherein the transport arm is configured to grip a frameless blank stored in one of the idle receptacles in the storage chamber and to move the frameless blank through the transfer opening into the work chamber;
a workpiece holder arranged in the work chamber and configured to receive the frameless blank from the transport arm, wherein the workpiece holder is configured to grip the frameless blank by a receiving rim of the frameless blank, and wherein the workpiece holder, for milling the frameless blank in the work chamber by a milling tool, is configured to hold by a clamping action the frameless blank at the receiving rim;
wherein the transport arm accesses the frameless blank in a vertical direction from a position above the idle receptacle, wherein the transport arm is configured to pivot together with the frameless blank gripped by the transport arm into a horizontal position, and wherein the transport arm is configured to move horizontally toward the workpiece holder in the work chamber for transferring the frameless blank to the workpiece holder.

9. A dental milling machine comprising:
a storage chamber;
idle receptacles arranged in the storage chamber and configured to store a plurality of blanks, wherein the plurality of blanks each are placed without frame as a frameless blank into the idle receptacles;
a transfer device arranged in the storage chamber and comprising a transport arm;
a work chamber adjoining the storage chamber;
a transfer opening arranged between the work chamber and the storage chamber;
wherein the transport arm is configured to grip a frameless blank stored in one of the idle receptacles in the storage chamber and to move the frameless blank through the transfer opening into the work chamber;
a workpiece holder arranged in the work chamber and configured to receive the frameless blank from the transport arm, wherein the workpiece holder is configured to grip the frameless blank by a receiving rim of the frameless blank, and wherein the workpiece holder, for milling the frameless blank in the work chamber by a milling tool, is configured to hold by a clamping action the frameless blank at the receiving rim;
wherein the transfer opening comprises a changeover flap and wherein the changeover flap opens when the transport arm pivots into a horizontal position.

10. The dental milling machine according to claim 1, wherein the workpiece holder comprises clamping jaws, wherein the receiving rim is provided on an outer circumference of the frameless blank, wherein the receiving rim is clamped between the clamping jaws, and wherein the clamping jaws provide the clamping action holding the frameless blank during milling.

11. A dental milling machine comprising:
a storage chamber;
idle receptacles arranged in the storage chamber and configured to store a plurality of blanks, wherein the plurality of blanks each are placed without frame as a frameless blank into the idle receptacles;
a transfer device arranged in the storage chamber and comprising a transport arm;
a work chamber adjoining the storage chamber;
a transfer opening arranged between the work chamber and the storage chamber;
wherein the transport arm is configured to grip a frameless blank stored in one of the idle receptacles in the storage chamber and to move the frameless blank through the transfer opening into the work chamber;
a workpiece holder arranged in the work chamber and configured to receive the frameless blank from the transport arm, wherein the workpiece holder is configured to grip the frameless blank by a receiving rim of the frameless blank, and wherein the workpiece holder, for milling the frameless blank in the work chamber by a milling tool, is configured to hold by a clamping action the frameless blank at the receiving rim;
wherein the workpiece holder comprises clamping jaws, wherein the receiving rim is provided on an outer circumference of the frameless blank, wherein the receiving rim is clamped between the clamping jaws, and wherein the clamping jaws provide the clamping action holding the frameless blank during milling;
wherein the workpiece holder comprises at least one clamping spring arranged between the clamping jaws and configured to apply a clamping force for producing the clamping action.

12. The dental milling machine according to claim 11, wherein a controlled counterforce is provided for cancelling the clamping force of the clamping jaws.

13. The dental milling machine according to claim 12, wherein the workpiece holder comprises a setting piston, wherein the controlled counterforce is a pneumatic force applied by the setting piston.

14. A dental milling machine comprising:
a storage chamber;

idle receptacles arranged in the storage chamber and configured to store a plurality of blanks, wherein the plurality of blanks each are placed without frame as a frameless blank into the idle receptacles;

a transfer device arranged in the storage chamber and comprising a transport arm;

a work chamber adjoining the storage chamber;

a transfer opening arranged between the work chamber and the storage chamber;

wherein the transport arm is configured to grip a frameless blank stored in one of the idle receptacles in the storage chamber and to move the frameless blank through the transfer opening into the work chamber;

a workpiece holder arranged in the work chamber and configured to receive the frameless blank from the transport arm, wherein the workpiece holder is configured to grip the frameless blank by a receiving rim of the frameless blank, and wherein the workpiece holder, for milling the frameless blank in the work chamber by a milling tool, is configured to hold by a clamping action the frameless blank at the receiving rim;

wherein the workpiece holder comprises a stationary clamping jaw and a moveable clamping claw supported on the stationary clamping jaw.

15. The dental milling machine according to claim 14, wherein the workpiece holder further comprises one or more actuating cylinders arranged in the stationary clamping jaw and operatively connected to the clamping claw, one or more guiding elements arranged in the stationary clamping jaw and operatively connected to the clamping claw, and one or more force storage devices arranged in the stationary clamping jaw and operatively connected to the clamping claw.

16. The dental milling machine according to claim 15, wherein the actuating cylinders, the guiding elements, and the force storage devices each are component groups that are functionally separate from each other.

17. The dental milling machine according to claim 15, wherein the actuating cylinders each have correlated therewith one of the guiding elements and one of the force storage devices.

18. The dental milling machine according to claim 15, wherein the clamping claw is held, guided, and actuated by a plurality of the actuating cylinders, a plurality of the guiding elements, and a plurality of the force storage devices.

19. The dental milling machine according to claim 18, wherein the plurality of the guiding elements are positioned on a first common circular arc and the plurality of the force storage devices are positioned on a second common circular arc, wherein the plurality of the actuating cylinders are arranged in an annular section defined between the first and second common circular arcs.

20. The dental milling machine according to claim 18, wherein, in an area between two of the actuating cylinders, two of the guiding elements and two of the force storage devices are arranged, respectively.

* * * * *